(12) United States Patent
Jessup et al.

(10) Patent No.: US 8,865,928 B2
(45) Date of Patent: Oct. 21, 2014

(54) PROCESS FOR REMOVING DIOXANE FROM A COMPOSITION

(71) Applicant: The Chemithon Corporation, Seattle, WA (US)

(72) Inventors: Walter A. Jessup, Seattle, WA (US); Burton Brooks, Bellevue, WA (US); W. Brad Sheats, Federal Way, WA (US)

(73) Assignee: The Chemithon Corporation, Seattle, WA (US)

( * ) Notice: Subject to any disclaimer, the term of this patent is extended or adjusted under 35 U.S.C. 154(b) by 0 days.

(21) Appl. No.: 14/048,600

(22) Filed: Oct. 8, 2013

(65) Prior Publication Data

US 2014/0100382 A1 Apr. 10, 2014

Related U.S. Application Data

(63) Continuation of application No. PCT/US2013/063712, filed on Oct. 7, 2013.

(60) Provisional application No. 61/711,190, filed on Oct. 8, 2012.

(51) Int. Cl.
*C07C 303/44* (2006.01)
*B01D 1/22* (2006.01)

(52) U.S. Cl.
CPC .............. *C07C 303/44* (2013.01); *B01D 1/227* (2013.01); *B01D 1/22* (2013.01); *B01D 1/223* (2013.01)
USPC ........................................................ 558/34

(58) Field of Classification Search
USPC ........................................................ 558/34
See application file for complete search history.

(56) References Cited

U.S. PATENT DOCUMENTS

| | | | |
|---|---|---|---|
| 4,285,881 A | 8/1981 | Yang | |
| 4,405,799 A | 9/1983 | Chakrabarti et al. | |
| 5,052,122 A | 10/1991 | Ishikawa et al. | |
| 5,446,188 A | 8/1995 | Gruber et al. | |
| 5,723,433 A | 3/1998 | Duvall et al. | |
| 5,857,269 A | 1/1999 | Vashitz et al. | |
| 6,058,623 A | 5/2000 | Brooks et al. | |

FOREIGN PATENT DOCUMENTS

| | | |
|---|---|---|
| CA | 2131216 C | 3/1995 |
| CN | 1345719 A | 4/2002 |
| CN | 1125813 C | 10/2003 |
| CN | 101690875 B | 8/2012 |
| CN | 102295767 B | 9/2012 |
| DE | 33 43 802 A1 | 6/1985 |
| EP | 0 645 445 B1 | 5/2000 |
| EP | 0 939 287 B1 | 9/2003 |
| EP | 1 191 091 B1 | 5/2004 |
| JP | 63-246357 | 10/1988 |
| JP | 11-314001 | 11/1999 |
| WO | WO-95/14660 A1 | 6/1995 |
| WO | WO-02/081381 A1 | 10/2002 |
| WO | WO-2005/087909 A1 | 9/2005 |

OTHER PUBLICATIONS

Farn, Chemistry and Technology of Surfactants, Blackwell Publishing, pp. 113-120 (2006).
Perry's Chemical Engineers' Handbook, Seventh Edition, 6-12 to 6-13 (1997).
Perry's Chemical Engineers' Handbook, Sixth Edition, 5-25, Table 5-8 (1984).
International Search Report and Written Opinion for Application No. PCT/US2013/063712, dated Jan. 28, 2014.

*Primary Examiner* — Kristin Vajda
(74) *Attorney, Agent, or Firm* — Marshall, Gerstein & Borun LLP

(57) ABSTRACT

Apparatus and processes for removing dioxane from a composition, e.g., an ethoxylated fatty alcohol sulfate paste, utilize an evaporator having an inlet chamber and one or more heated channels. The process includes the step of heating the composition at a location upstream of the flow restriction to a temperature above the flashing temperature of water at a pressure of the channel inlet and applying a pressure to the heated composition to avoid such flashing. The process further includes the step of passing the pressurized, heated composition through the evaporator. The process can further include injecting a vapor into the channel. The purified, concentrated product can be diluted with water to a desired concentration.

41 Claims, 17 Drawing Sheets

| Ex. # | Tube Length ft | AES type cation/ moles EO | Feed As is lb/hr | Feed 100% active basis lb/hr | Injection steam lb/hr | Feed out preheater °F | Jacket Jac | jacket °F | Flash tank vapor °F | Flash tank vapor Torr | Feed active % | Product active % | Delta active % |
|---|---|---|---|---|---|---|---|---|---|---|---|---|---|
| 1 | 10+10 | Na/3 | 90 | 62 | 42 | 240 | Stm | 242 | 153 | 149 | 69.3 | 87.1 | 17.9 |
| 2 | 10+10 | Na/3 | 90 | 62 | 42 | 262 | Stm | 263 | 160 | 149 | 69.3 | 91.7 | 22.5 |
| 3 | 10 | Na/3 | 150 | 109 | 75 | 201 | TW | 207 | 156 | 150 | 72.8 | 79.0 | 6.2 |
| 4 | 10 | Na/3 | 150 | 109 | 75 | 217 | TW | 223 | 154 | 150 | 72.8 | 81.9 | 9.1 |
| 5 | 10 | Na/3 | 150 | 109 | 75 | 183 | TW | 192 | 150 | 148 | 72.8 | 76.7 | 4.0 |
| 6 | 10 | Na/3 | 100 | 72 | 44 | 206 | TW | 206 | 153 | 149 | 72.4 | 80.5 | 8.0 |
| 7 | 10 | Na/3 | 100 | 72 | 44 | 221 | TW | 221 | 153 | 150 | 72.4 | 83.6 | 11.2 |
| 8 | 10 | Na/3 | 100 | 72 | 44 | 188 | TW | 189 | 148 | 149 | 72.4 | 77.5 | 5.1 |
| 9 | 10 | Na/3 | 150 | 109 | 75 | 220 | TW | 224 | 165 | 148 | 72.4 | 81.2 | 8.8 |
| 10 | 10 | Na/3 | 150 | 109 | 75 | 204 | TW | 205 | 159 | 151 | 72.4 | 78.0 | 5.6 |
| 11 | 10 | Na/3 | 150 | 109 | 75 | 187 | TW | 190 | 155 | 150 | 72.4 | 76.2 | 3.7 |
| 12 | 10 | Na/3 | 150 | 119 | 30 | 217 | Stm | 241 | 158 | 150 | 79.2 | 91.1 | 12.0 |
| 13 | 10 | Na/2.5 | 150 | 111 | 30 | 214 | Stm | 232 | 165 | 148 | 73.9 | 87.6 | 13.7 |
| 14 | 10 | Na/3 | 150 | 106 | 15 | 240 | Stm | 241 | 170 | 150 | 70.8 | 84.7 | 14.0 |
| 15 | 10 | Na/3 | 150 | 106 | 30 | 242 | Stm | 241 | 167 | 151 | 70.8 | 85.1 | 14.4 |
| 16 | 10 | Na/3 | 150 | 106 | 0 | 242 | Stm | 241 | 154 | 150 | 70.8 | 81.1 | 10.3 |
| 17 | 10 | Na/3 | 150 | 106 | 30 | 241 | Stm | 240 | 160 | 150 | 70.8 | 84.7 | 14.0 |

Stm = steam, TW = tempered water, EO = moles of ethylene oxide polymerized onto one mole of fatty alcohol

Fig. 17a

| Ex. # | Feed water % | Product water % | Feed 1,4-dioxane 100% active basis ppm | Product 1,4-dioxane 100% active basis ppm | 1,4-dioxane In/Out 100% active basis ppm to ppm ratio | Injection steam to feed 100% active basis mass ratio | Water evaporated from feed 100% active basis mass ratio | Total water vapor to feed 100% active basis mass ratio |
|---|---|---|---|---|---|---|---|---|
| 1 | 28.7 | 10.2 | 82.2 | 1.8 | 45.7 | 0.67 | 0.26 | 0.93 |
| 2 | | 5.3 | | 0.8 | 102.8 | 0.67 | 0.32 | 1.00 |
| 3 | | 19.0 | | 5.0 | 13.4 | 0.69 | 0.09 | 0.77 |
| 4 | 25.5 | 17.1 | 67.0 | 3.5 | 19.1 | 0.69 | 0.12 | 0.81 |
| 5 | | 21.7 | | 4.9 | 13.7 | 0.69 | 0.05 | 0.74 |
| 6 | | 17.8 | | 5.8 | 6.4 | 0.61 | 0.11 | 0.72 |
| 7 | | 15.0 | | 3.3 | 11.2 | 0.61 | 0.15 | 0.76 |
| 8 | 26.0 | 21.0 | 37.0 | 5.6 | 6.6 | 0.61 | 0.07 | 0.68 |
| 9 | | 17.1 | | 2.5 | 14.8 | 0.69 | 0.12 | 0.81 |
| 10 | | 20.0 | | 3.2 | 11.6 | 0.69 | 0.08 | 0.77 |
| 11 | | 22.2 | | 4.6 | 8.0 | 0.69 | 0.05 | 0.74 |
| 12 | 19.4 | 7.1 | 44.5 | 0.9 | 49.4 | 0.25 | 0.15 | 0.40 |
| 13 | 23.7 | 10.1 | 21.6 | 1.3 | 19.8 | 0.27 | 0.19 | 0.46 |
| 14 | | 11.7 | | 6.6 | 12.7 | 0.14 | 0.20 | 0.34 |
| 15 | 26.2 | 11.0 | 83.6 | 3.3 | 25.3 | 0.28 | 0.20 | 0.49 |
| 16 | | 13.2 | | 11.6 | 7.2 | 0.00 | 0.15 | 0.15 |
| 17 | | 10.4 | | 3.1 | 27.0 | 0.28 | 0.20 | 0.48 |

Stm = steam, TW = tempered water, EO = moles of ethylene oxide polymerized onto one mole of fatty alcohol

Fig. 17b

PROCESS FOR REMOVING DIOXANE FROM A COMPOSITION

CROSS-REFERENCE TO RELATED APPLICATION

This is a continuation of International Application No. PCT/US13/63712 filed Oct. 7, 2013, and the benefit under 35 U.S.C. §119(e) of U.S. Provisional Patent Application Ser. No. 61/711,190 filed Oct. 8, 2012 is also claimed, and the disclosures thereof are hereby incorporated by reference herein.

BACKGROUND OF THE INVENTION

1. Field of the Invention

The invention relates generally to processes and apparatus for removing dioxane components from materials such as solutions, dispersions, slurries, emulsions, and pastes. More particularly, the invention relates to processes that can remove 1,4-dioxane from alkoxylated fatty alcohol sulfate pastes to a level previously not possible.

2. Description of Related Technology

Detergent products contain surface active ingredients (sometimes referred to as "detergent active ingredients" or "detergent actives"), which may be neutralized salts of acids produced, for example, by sulfating or sulfonating $C_8$-$C_{20}$ organic materials and, preferably, $C_{11}$-$C_{18}$ organic materials, such as, for example, fatty alcohols, alkoxylated fatty alcohols, ethoxylated fatty alcohols, alkyl benzenes, alpha olefins, methyl esters, alkyl phenol alkoxylates, and alkyl phenol ethoxylates. The process of making detergent actives from the acid form is typically performed in a solvent, such as water and/or alcohol. The resulting detergent material may be a paste, a solution, or a slurry of various components. (The term detergent "paste" as used hereinafter is meant to include detergent solutions, slurries and pastes). Final detergent products are made from such detergent pastes.

Fatty alcohol ethoxy sulfates (AES) is a mild surfactant that generates considerable foam and has excellent degreasing properties. It is used in personal care products, such as shampoo, and liquid dish cleaners, for example. Since it is derived from fatty alcohol it can be made from natural oils, for example coconut oil.

1,4-dioxane is a by-product formed during the sulfation process of making fatty alcohol alkoxy sulfates and AES in relatively small amounts and that remains in the sulfated product. Consumer protection groups have become concerned about 1,4-dioxane in products including baby shampoo, for example. The U.S. Environmental Protection Agency classifies dioxane as a probable human carcinogen, and in California it is "classified to cause cancer" and has come under increasing scrutiny by consumer groups and regulatory bodies. Presently, there are no regulatory limits on the amount of 1,4-dioxane that is safe in these products; but some companies have started implementing their own quality standards. There is thus a need for minimizing 1,4-dioxane in sulfated products.

Technology for minimizing 1,4-dioxane formation has been reported in the literature dating back decades. Prior studies report steps that can be taken in the sulfation process to minimize the amount of 1,4-dioxane that forms. Reducing the $SO_3$ gas concentration from 4% to 2.5%, for example, has a dramatic effect and cuts the amount of 1,4-dioxane that forms in half. Less dramatic benefits come from running at low mole ratios of $SO_3$:feed so that conversion of the feed to the sulfated product is less complete. These changes have a dramatic impact on the production capacity and cost-efficiency of a sulfation plant. Moves such as these cut the plant capacity by as much as 50%.

SUMMARY OF THE INVENTION

According to a process of the invention, a method of removing dioxane from a paste includes pumping a dioxane-containing aqueous paste feedstock to an inlet of an evaporator, supplying heat to the paste in the evaporator, and reducing the vapor pressure in the evaporator, to vaporize dioxane and water from the paste and thereby concentrate the paste, and collecting the resulting concentrated product. The concentrated product can be diluted with water to a desired final concentration, e.g. in a range of about 65 wt. % to about 80 wt. % active sulfate, or 65 wt. % to about 76 wt. % active sulfate. The pH of the concentrated and/or diluted product can be adjusted with a neutralizing agent, including a caustic agent or a buffering agent.

In a process described herein, the feedstock paste optionally can be an ethoxylated fatty alcohol sulfate paste.

In one aspect, the evaporator can include a heated channel. For example, with a channel the process can further include preheating the dioxane-containing paste feedstock to a temperature wherein water would flash from the paste, and selectively applying pressure to the paste to avoid vaporization of water; pumping the paste to an inlet of the channel under a pressure selected to avoid flashing of water; introducing the paste into the channel; supplying heat to the paste in the channel and selectively reducing the pressure along the channel resulting in the flashing of dioxane and water components of the paste, wherein vapor liberated during the flashing acts as a motive force to move the increasingly viscous paste along the channel; collecting the resulting concentrated product and vaporized dioxane and water components in a separation vessel disposed downstream of an outlet of the channel, wherein the separation vessel operates at a pressure less than an operating pressure of the outlet of each channel; and venting the vaporized dioxane and water components from the separation vessel from an overhead vapor outlet and discharging the residual paste composition from the bottom of the separation vessel.

In another aspect, the evaporator vessel can include an agitator. For example, the evaporator can be a wiped film evaporator.

In a process described herein, the process optionally can be performed in the absence of injecting a vapor into the evaporator. In such embodiments, the temperature of the feedstock can be relatively high, for example in a range of about 200° F. to 265° F. (93° C. to 129° C.), for example 240° F. (116° C.). In such embodiments, further optionally heat can be supplied to the paste in the evaporator (e.g. channel or channels) by providing a heat jacket around the evaporator. The heat jacket can be operated at a temperature in a range of about 200° F. to 265° F. (93° C. to 129° C.), for example 240° F. (116° C.).

In a process described herein, the process optionally can be performed with further injecting a vapor into the evaporator or channel while introducing the paste into the evaporator or channel. In such embodiments, optionally the vapor can be steam. For example, Further optionally, the feedstock temperature can be in a range of about 185° F. to about 200° F. (85° C. to 93° C.). Still further optionally, the feedstock paste can be an ethoxylated fatty alcohol sulfate paste and the mass ratio of injected steam to active ethoxylated fatty alcohol sulfate can be in a range of 0.1 to 1.

In a process described herein, the process optionally can be performed wherein the separation vessel operates at a pressure of less than 1 bar absolute, optionally in a range of 50 Torr to 300 Torr or 100 Torr to 300 Torr, or 50 Torr to 200 Torr, or 50 Torr to 100 Torr.

In a process described herein, the process optionally can be performed with preheating the feedstock paste prior to introducing the paste into the evaporator to a selected temperature to result in the flashing of water from the paste at an operating pressure of an inlet of the evaporator.

In a process described herein, the process optionally can be performed with a stripper/dryer which includes a plurality of channels and wherein the feedstock paste is introduced into each of the channels for processing.

In a process described herein, the process optionally can be performed with a stripper/dryer having an inlet chamber, a plurality of channels, and a plurality of flow restrictions, each of the channels having an inlet operating at a pressure, each flow restriction disposed between the stripper/dryer inlet chamber and one cooperating channel, the flow restriction being immediately upstream of the cooperating channel inlet with respect to a direction of flow of the composition through the stripper/dryer.

In a process described herein, the process optionally can be performed with further collecting the purified, concentrated product from the separation vessel and diluting the product with water.

In a process described herein, the process optionally can be performed with a feedstock paste including an ethoxylated fatty alcohol sulfate paste including 65 wt. % to 75 wt. % active ethoxylated fatty alcohol sulfate.

In a process described herein, the process optionally can be performed to yield a concentrated product including 80 wt. % to 95 wt. % solids, or 80 wt. % to 95 wt. % active component of the solids (e.g., AES).

In a process described herein, the process optionally can be performed to yield a concentrated product including 76 wt. % to 99 wt. % active ethoxylated fatty alcohol sulfate, or 80 wt. % to 99 wt. % active ethoxylated fatty alcohol.

In a process described herein, the process optionally can be performed to yield a wt. % increase of the active sulfonate following concentration, based on the total weight of the paste, of at least 5 wt. %, or at least 10 wt. %.

In a process described herein, optionally the concentrated product can include 3-mol ethoxylated fatty alcohol sulfate and the concentrated product can include 76 wt. % to 88 wt. % active, or 80 wt. % to 88 wt. % active.

In a process described herein, optionally the concentrated product can include 7-mol ethoxylated fatty alcohol sulfate and the concentrated product can include 76 wt. % to 95 wt. % active, or 80 wt. % to 95 wt. % active.

In a process described herein, the process optionally can be performed to yield a dioxane reduction ratio of at least 7:1, or greater than 7:1.

In a process described herein, the process optionally can be performed to yield a dioxane content of the concentrated product of less than 20 ppm on 100% active matter basis.

In a process described herein, the process optionally can be performed to yield a concentrated product having a water content of 25 wt. % or less, or 15 wt. % or less, or 5 wt. % or less, or 2 wt. % or less.

In a process described herein, the process optionally can be performed to remove a dioxane component which is 1,4-dioxane.

The process can further include sulfating an alkoxylated fatty alcohol with a sulfur trioxide gas concentration of greater than 2.5%, to produce the alkoxylated fatty alcohol sulfate paste.

The process can optionally include the step of sulfating an alkoxylated fatty alcohol with a mole ratio of sulfur trioxide gas to alkoxylated fatty alcohol that is relatively high, e.g., at least 1.00, or at least 1.03, or at least 1.04, for example in a range of 1.00 to 1.05 or 1.03 to 1.05, to produce the alkoxylated fatty alcohol sulfate paste.

For the methods, apparatus, and compositions described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description, taken in conjunction with the drawings. While the method, apparatus, and compositions are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

FIGS. 17a and 17b are tables showing conditions and results of dioxane removal by various methods according to the invention.

DETAILED DESCRIPTION OF THE INVENTION

Figure 1:
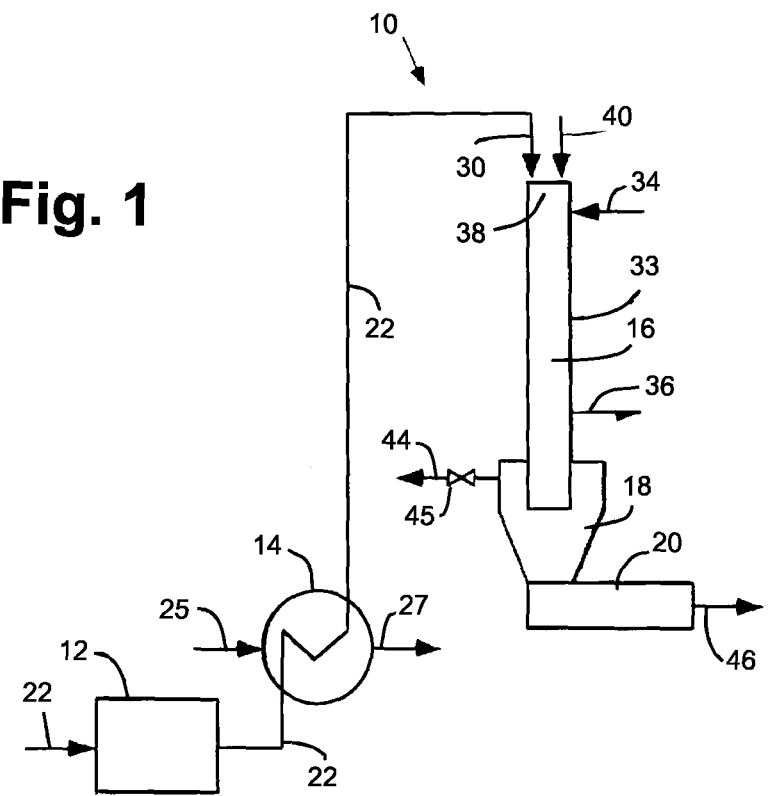
FIG. 1 is a process flow diagram illustrating a solvent removal system for use in the process according to the invention.

Sulfated alkoxylated alcohols and AES exhibit complicated fluid properties as their concentrations are varied in an aqueous solution. Most consumer products use AES in a low concentration range up to about 15 to 20% by weight (wt. %), and generally less. In this concentration range the solution is an ordinary Newtonian fluid. As the concentration of AES is increased, at about 28 wt. % and just over for 3-mole AES, a phase transition begins. As the concentration is increased over about 28 wt. %, the viscosity becomes extremely high and the AES paste in this middle concentration range (e.g., about 30 wt. % to about 68 wt. %) acts as a gel or semi-solid, and is impractical to handle. However, in the vicinity of 70 wt.

% AES the viscosity surprisingly is reduced and a manageable fluid phase occurs. This concentrated paste form is preferred by sulfation plant operators who want to transport this product in a concentrated form. At concentrations greater than 70 wt. %, the viscosity of the paste gradually increases again, so that making a concentration greater than 70 wt. % is possible and may, in some cases, be preferred.

Alkoxylated fatty alcohols are not "pure" materials but are mixtures of homologous molecules that contain different amounts of ethylene oxide, for example. The addition of ethylene oxide into fatty alcohols has long been done to produce nonionic surfactants. These have many uses in consumer products. A typical nonionic ethoxylated fatty alcohol (AE) can be referred to as a nominal "3-mole AE", meaning that it has on average 3 moles of ethylene oxide added into it. In fact the product will contain some of the primary alcohol with no EO added, some 1-EO, some 2-EO, some 3-EO, some 4-EO and so forth up the homologous series. Thus, most manufacturers name their AE by describing the fatty alcohol and the average number of EO added. The amount of 1,4-dioxane that forms upon sulfation with air-$SO_3$ gas increases with the EO content of the AE feed. To minimize the formation of 1,4-dioxane some manufacturers have decided to shift the average EO content to a number less than 2 in an attempt to reduce the amount of 1,4-dioxane that forms. This choice may result in avoidance of forming 1,4-dioxane, while a better-performing surfactant product would have a higher EO content in the AES.

The present inventors recognized that modifying the sulfation process to try to reduce the amount of 1,4-dioxane would not efficiently provide the means to eliminate 1,4-dioxane or to reduce it to an insignificant concentration; instead, the present inventors created a process and embodiments of suitable apparatus to physically and selectively remove 1,4-dioxane from the AES following sulfation, and prior to final product formulation when a dilute product is desired.

According to the principle of the invention, a paste mixture containing dioxane is caused to come into equilibrium with a vapor stream so that part of the dioxane is transferred to the vapor phase. The vapor phase and the paste are then mechanically separated, thereby reducing the dioxane in the paste.

A method of removing dioxane from a paste can include pumping a dioxane-containing aqueous paste feedstock to an inlet of an evaporator, supplying heat to the paste in the evaporator, and reducing the vapor pressure in the evaporator, to vaporize dioxane and water from the paste and thereby concentrate the paste, and collecting the resulting concentrated product.

The evaporator can be any suitable evaporator. Evaporators include tubular evaporators (horizontal and vertical), forced circulation tubular evaporators, falling film evaporators, rising/falling film evaporators, gasketed plate evaporators, and agitated thin-film evaporators (e.g. wiped film evaporators).

In one type of embodiment, the evaporator is a wiped film evaporator.

In another type of embodiment, the evaporator is a channel. In such an embodiment, a method of removing dioxane from a paste can include:

(a) preheating a dioxane-containing sulfate paste feedstock to a temperature wherein water would flash from the paste and selectively applying pressure to the paste to avoid vaporization of any of the components of the paste;

(b) pumping the paste to an inlet of a dryer under a pressure selected to avoid flashing of any of the components of the paste, the dryer having at least one channel;

(c) introducing the paste into the channel;

(d) supplying heat to the paste in the channel and selectively reducing the pressure along the channel resulting in the flashing of dioxane and water components of the paste wherein vapor liberated during the flashing acts as a motive force to move the increasingly viscous paste along the channel;

(e) collecting the resulting concentrated product and vaporized dioxane and water components in a separation vessel disposed downstream of an outlet of the channel, wherein the separation vessel operates at a pressure less than an operating pressure of the outlet of each channel; and (f) venting the vaporized dioxane and water components from the separation vessel.

The apparatus, method, and compositions used and produced are contemplated to include embodiments including any combination of one or more of the additional optional elements, features, and steps further described below (including those shown in the figures), unless stated otherwise.

As used herein, the term "comprising" indicates the potential inclusion of other agents, elements, steps, or features, in addition to those specified.

In the following description, the feedstock is described with respect to neutralized AES as an example, although other dioxane-containing feedstocks can be used.

In the following description, the primary dioxane component referred to is 1,4-dioxane, although other dioxane isomers are also contemplated. Thus the dioxane component can include one or more of 1,2-dioxane, 1,3-dioxane, and 1,4-dioxane.

In the following description, steam is described as the vapor for use in the optional injection of a vapor into the evaporator, although other vapor compositions can be used. The amount of dioxane reduction when stripping with air is a function of the ratio of the vapor pressure of dioxane divided by the total pressure of the system. Considering the thermal stability of the active, dioxane at reasonable temperatures only has a vapor pressure of a couple hundred mmHg and the reduction ratio will be reduced by a factor of four if operated at atmospheric pressure, therefore the system should operate under a vacuum. A vacuum pump large enough to compress the volume of air required for a significant dioxane reduction ratio would be prohibitive compared to a condensable injection vapor such as steam. Thus, preferably the injection vapor is an easily condensable vapor, preferably steam. Additionally, if dioxane is being stripped, then so will the water since its vapor pressure is similar to dioxane.

The preferred injection vapor thus is steam, but the system needs to operate at a vacuum to control the temperature. Steam can be condensed before the vacuum pump so that the pump is sized for any non-condensables that leak into the system, a much more economical system compared to stripping with air. Since the system will be operating under a vacuum, a pumping system is required to discharge the paste from a vacuum.

As mentioned above, the undesirable byproduct, 1,4-dioxane, is made during the sulfation process. A proposed mechanism for the formation of 1,4-dioxane is for a molecule of ethoxysulfuric acid to form a complex with a molecule of $SO_3$. A rearrangement occurs, forming a new ethoxysulfuric acid with two fewer ethylene oxide equivalent units and 1,4-dioxane which is complexed with an $SO_3$. The $SO_3$ can be released from the 1,4-dioxane and react to form ethoxysulfuric acid or recycle through this process and generate another molecule of 1,4-dioxane.

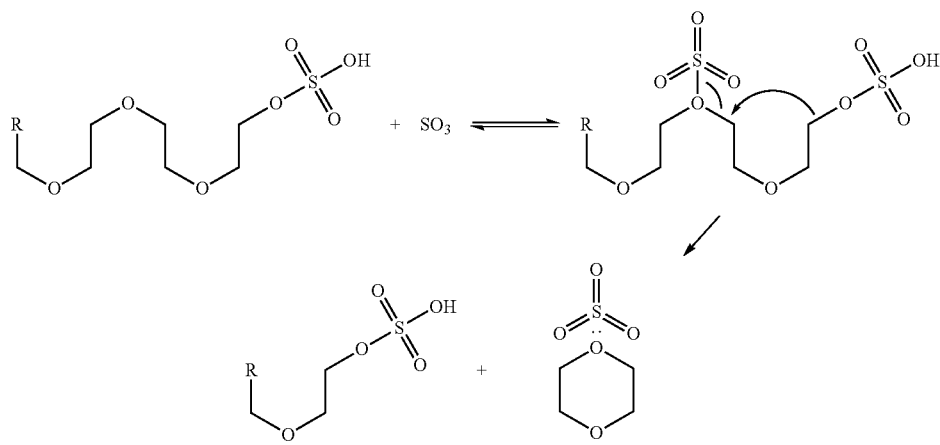

It is generally accepted that dioxane is formed during sulfation only when there are three or more moles of ethoxylation per alcohol molecule. By extension, if the feedstock has two moles or less of ethoxylation, dioxane should not be formed. However, as mentioned above, the distribution of ethoxylates on each molecule is not uniform, so even though the average may be two moles, there will be some molecules with three or more ethoxylates, and therefore dioxane is formed even when the average degree of ethoxylation is two moles or less.

The inlet paste feedstock concentration typically made commercially is either the diluted form at 28-30 wt. % (typically 28 wt. %) AES, or the concentrated form at about 70 wt. % AES. In the present method, any suitable concentration of feedstock can be used as long as the viscosity renders it pumpable, for example in the range of 20 wt. % to 85 wt. % active, and preferably the feedstock concentration will be at or near a concentration which corresponds to a local viscosity minimum. Thus, the feedstock can be at or near a concentration which corresponds to a lower local viscosity minimum, e.g., in a range of about 28 wt. % to about 30 wt. % active. In another embodiment, feedstock can be at or near a concentration which corresponds to a higher local viscosity minimum, e.g., in a range of about 68 wt. % to about 75 wt. % active. A range of 65 wt. % to about 85 wt. % active is also contemplated. It was discovered that dioxane removal is improved when the paste has a relatively low water content. A water content of less than 25 wt. %, or in a range of about 5 wt. % to about 25 wt. % out of the stripper/dryer is particularly contemplated to achieve very high dioxane removal rates with a minimum external steam requirement and creating a paste that is still manageable to handle, for example in the equipment described herein. Thus, the system is also contemplated to include a neutralization system upstream of the preheater and related pump, and preferably a High Active Neutralizer that will make about 70% active AES paste as a feed to a system such as the type shown in FIGS. 1-5.

In a process described herein, the process can be performed to yield a wt. % increase of the active sulfonate following concentration, based on the total weight of the paste, of at least 5 wt. %, or at least 6 wt. %, or at least 7 wt. %, or at least 8 wt. %, or at least 9 wt. %, or at least 10 wt. %, or at least 12 wt. %, or at least 15 wt. %, or more.

The mass flow rate of the "as is feed" plays a role in the distribution of the feed material into the channel or channels of the tube or tubes of an apparatus which includes such features. There is a pressure drop as the feed material is forced through a series of orifices, as described below. The steam is provided to each tube through a similar pressure manifold, so that the mass of inlet feed and the mass of steam are substantially equal in all tubes. The paste is atomized and a high velocity turbulent flow regime is set up inside the contacting tubes. The vapor velocity imparts shear to the fluid reducing its apparent viscosity so that the paste forms a very thin film on the tube wall. The thinner film requires very little time to reach equilibrium, and since the steam is in a very turbulent state the dioxane is quickly dispersed in the vapor phase, resulting in a near approach to equilibrium. The system can be designed to have no mechanical seals or moving parts other than the discharge pump and vacuum system, making it very reliable.

The evaporator apparatus operates in a co-current configuration in that the feed and vapor stripping media are introduced together at the top of the tube or tubes, for example, and travel down to a separation vessel in intimate contact. The length of the tube and velocity of the two phases determine the time for equilibrium to be reached between the two phases. There is a limit to the length of the tube in that as the tube is lengthened the pressure drop accumulates until the pressure at the inlet of the tube becomes high enough to condense the injection steam and form gels with high active feed. Under the preferred conditions described herein, the equilibrium separation occurs very quickly. A tube length of about 10 feet (3 meters) is suitable to provide adequate contacting time for separation of the dioxane under a broad range of conditions, and thus tube lengths in a range of about 6 feet (about 2 meters) to about 20 feet (6 meters) are expected to be suitable for a broad variety of pastes and operating conditions, optionally 2 meters to 4 meters, although the invention is not limited to any particular tube length.

A preferred wiped film evaporator is the top vapor exit form, where the paste is fed in to the top and the vapor exits from the top, giving a counter current flow. It is advantageous to operate the evaporator at the same conditions as the previously described multi-tube stripper, namely at a vacuum to lower the operating temperature. It is also advantageous to add steam near the paste product exit. It is also advantageous to use a rotor that partially fills the void in the evaporator to enhance contact between the steam and the paste.

"Dioxane Reduction Ratio" is defined herein as the ratio of dioxane concentration on 100% active basis in the feedstock paste compared to the product paste. A dioxane reduction ratio of 2:1 would mean for example that feed containing 100 ppm wt dioxane (on 100% active basis) would have 50 ppm dioxane as product from the process. The dioxane reduction ratio preferably is at least 4:1, or at least 5:1, or at least 6:1, or at least 7:1. According to the process described herein, dioxane reduction ratios of 20, 25, 30, 40 and more have been achieved. Material containing 80 ppm to 100 ppm of 1,4-dioxane has been purified down to approximately 1 ppm 1,4-dioxane in a single pass through the channel evaporator system described herein. The less water left in the product, the less dioxane remained as well. Thus, the process according to the description herein can provide a product with any desired limit of 1,4-dioxane, for example 20 ppm, less than 20 ppm, 10 ppm, less than 10 ppm, 5 ppm, less than 5 ppm, 1 ppm, or even less than 1 ppm, in a single pass. Multiple passes can also be employed, if desired. Likewise, parallel evaporator processing can also be employed, for example as described herein.

The process has been run with a variety of AES feeds including various EO mole ratios AES (sodium sulfate) pastes and 3-mol AES (ammonium sulfate) paste. Results indicate that the system is remarkably versatile and controllable. A particular paste matter can be characterized with a few experiments and the system conditions can be selected by the person of ordinary skill in the art in view of the teachings herein to make just about any desired reduction in 1,4-dioxane that is desired. The vapor/liquid equilibrium behavior of the composition may be determined in advance by laboratory measurements. From the measurements, it is possible to predetermine the boiling or flashing point of water and dioxane in the composition and thus determine target operating conditions. Preferably, a target temperature is determined which is significantly above the flashing temperature of water at the operating pressure of an evaporator (e.g., inlet stripper/dryer channel) but low enough so that the paste does not decompose.

A common feedstock material that can be used in the method described herein is sodium ethoxysulfate (AES) with 2.5 to 3 moles of ethoxylation with ethylene oxide (EO) per mole of fatty alcohol. The fatty alcohol carbon chain length is typically in the range of $C_{12}$ to $C_{16}$ and can be the made from a naturally occurring material or can be purely synthetic. The degree of ethoxylation with ethylene oxide can be in the range of 0.5 to 50 moles of EO to mole of fatty alcohol, for example in a range of 1 to 12, or 3 to 7, for the purposes of sulfation to ethoxysulfuric acid and subsequent neutralization of the acid. Neutralization can be with sodium, potassium and ammonium types (e.g., TEA) on anionic bases, for example. The molecular weight for example of a sodium ethoxysulfate (3 moles of EO) will be in the range of 442 Daltons. The process described herein for removing dioxane is not constrained by the source of the carbon chain, the degree of ethoxylation, or the neutralizing agent.

For the purposes of this discussion the feedstock is referenced to 100% active basis—active referring to for example sodium ethoxysulfate. Typical commercial sodium ethoxysulfate is produced as 70 wt. % active with the remainder being primarily water, and small amounts of unreacted ethoxylate, sodium sulfate, sodium hydroxide, sodium chloride, sodium carbonate, and sodium citrate. However, AES can be produced between 65 wt. % and 85 wt. % active and can be processed in the method and apparatus described herein. The feedstock active flow rate per evaporator or evaporator channel (loading) may be varied but is dependent on the channel diameter and viscosity of the feedstock material. The viscosity of the AES material is composition and temperature dependent.

As mentioned above, the process of drying the feedstock in the method described herein significantly decreases the 1,4-dioxane content of the product. Additional optional benefits which can be achieved in the method and apparatus described herein can include one or more of: reduction in one or more secondary components and/or contaminants (e.g., one or more of oils, esters, ketones and aldehydes), degassing, and deodorization of the AES.

A particular advantage of the apparatus and method described herein is the ability to add energy (heat) into the process when stripping. Without the ability to add heat, it would be difficult to operate on the upper level of the concentration curve since all processes lose some heat and as heat is lost some of the steam condenses, forming lower concentration paste. At the lower concentration range (e.g. 28 wt. % to 30 wt. %), this is acceptable since the paste's viscosity simply drops. However, at the higher concentration range gel particles can form, and the gel particles are very difficult to deal with in conventional stripping systems. With the apparatus and method described herein, additional heat can be added in order to avoid condensation (e.g. in the tubes of a tube-style evaporator).

There are three primary operating parameters influencing the reduction of the 1,4-dioxane content in the AES as it is processed in the method and apparatus described herein, and four primary operating parameters when the optional injection of a vapor into the evaporator is employed.

The first operating parameter is vacuum (pressure) level as measured in the collection/separation vessel (e.g. vessel 18, vessel 58, or evaporator 216 described below), such as a flash tank, at the end of the tube or bundle of tubes (e.g. elements 32 and 57 described below). As it will be understood, the collection vessel also operates as a separation vessel. This can range from 100 to 300 Torr, for example 150 Torr, wherein lower pressure increases the degree of drying.

The second operating parameter is the temperature in the evaporator (e.g. tubes), for example as influenced by the heating jacket temperature (e.g. jacket 33, jacket 88, or jacket 231 described below).

The third operating parameter is the paste feed temperature to the tubes. The paste feed temperature and jacket temperature can be set in tandem, or in the alternative can be different. When injecting steam, for example, the jacket and feed temperatures can be set to 185° F. (85° C.). As another example, when drying without using steam the jacket and feed temperatures can be set to 240° F. (116° C.), or in a range of about 200° F. to 265° F. (93° C. to 129° C.). Increasing temperature results in decreased water content in the concentrated product and decreased 1,4-dioxane content.

The fourth operating parameter is the injection steam to feed ratio, when used, for example a mass ratio of steam to total paste mass or active component mass. A mass ratio of steam to total paste mass in a range of about 0 to 1 or 0.1 to 1 can accommodate a range of feed stock conditions. A mass ratio of steam to active AES component mass in a range of about 0 to 1 or 0.1 to 1 is also contemplated. The ratio will influence the amount of dioxane removal, with higher ratios leading to more dioxane removal. Thus the particular ratio chosen can depend on the desired amount of 1,4-dioxane reduction. When drying is combined with the use of injection steam, the injection steam can be decreased accordingly, depending on the degree of 1,4-dioxane reduction desired. Optionally, the use of injection steam can be eliminated completely, resulting in a reduced amount of condensate required to be handled.

When drying is used alone or in combination with steam injection, the amount of 1,4-dioxane reduction ratio achieved has ranged from 5 to 100. In these cases the total amount of water vapor to feed active in the method has ranged from 0.1 to 1. A portion of the water vapor can be from the injection steam and a portion can be from the water evaporated from the process paste as it passes down the tubes.

If the AES is dried substantially, the material can be diluted back to the feed inlet concentration with water or as desired, for example corresponding to a lower local viscosity minimum around 25 wt. % to 28 wt. % active. AES material has been dried up 95 wt. % active in the channel apparatus and method described herein; for example, a 3 mole AES has been dried to 92 wt. % active or 95 wt. % solids. Functionally, the lower the remaining water content in the product, the greater the 1,4-dioxane reduction for the same energy consumption (e.g., heating steam, for example in a heating jacket and/or preheater). Thus, it is contemplated that the AES can be dried to at least 80 wt % active, or at least 85 wt. % active, or at least 86 wt. % active, or at least 87 wt. % active, or at least 88 wt. % active, or at least 89 wt. % active, or at least 90 wt. % active, or at least 91 wt. % active, or at least 92 wt. % active, for example. Similarly, it is contemplated that the AES can be dried to at least 83 wt % solids, or at least 88 wt. % solids, or at least 89 wt. % solids, or at least 90 wt. % solids, or at least 91 wt. % solids, or at least 92 wt. % solids, or at least 93 wt. % solids, or at least 94 wt. % solids, or at least 95 wt. % solids, for example. Following dioxane removal, additional end product components can be added to the paste, such as components that would have stripped out of the paste if they had been added earlier, for example ethanol.

Optionally, the process can further include sulfating an alkoxylated fatty alcohol with a sulfur trioxide gas concentration of greater than 2.5%, to produce the alkoxylated fatty alcohol sulfate paste. The concentration can be at least 3%, or greater than 3%, or at least 3.5%, or greater than 3.5% or at least 4%, or greater than 4%, for example. Increasing the sulfur trioxide concentration increases the amount of 1,4-dioxane that forms, but it also dramatically increases the yield of alkoxylated fatty alcohol sulfate paste. In the present method, it is contemplated to use a relatively high concentration of sulfur trioxide in the sulfation process to increase yield, and to use the concentrating method described above to remove 1,4-dioxane from the AES paste, to result in an overall process that is more efficient.

Similarly, the process can optionally include the step of sulfating an alkoxylated fatty alcohol with a mole ratio of sulfur trioxide gas to alkoxylated fatty alcohol that is relatively high, e.g., at least 1.00, or at least 1.03, or at least 1.04, for example in a range of 1.00 to 1.05 or 1.03 to 1.05, so that the conversion of the alkoxylated fatty alcohol feed to AES is more complete, to produce the alkoxylated fatty alcohol sulfate paste. Increasing the mole ratio of sulfur trioxide gas to alkoxylated fatty alcohol in the sulfation process increases the amount of 1,4-dioxane that forms, but it also increases the yield of alkoxylated fatty alcohol sulfate paste. In the present method, it is contemplated to use a relatively high mole ratio of sulfur trioxide gas to alkoxylated fatty alcohol in the sulfation process to increase yield, and to use the concentrating method described above to remove 1,4-dioxane from the AES paste, to result in an overall process that is more efficient.

Figure 2:
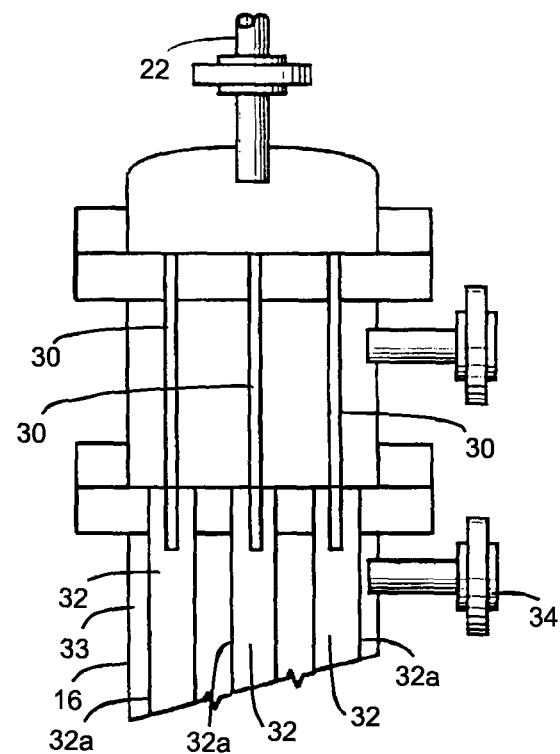
FIG. 2 is a partial, sectional view of a solvent removal apparatus for use in the process according to the invention.

A process according to the invention is further illustrated in FIG. 1 in which the dioxane removal system generally designated 10 comprises an inlet pump 12, a pre-heater 14, a stripper/dryer 16, a collection vessel 18 and an outlet means such as a plodder, extruder or pump 20. In most cases, a pump will be adequate. FIG. 2 depicts the stripper/dryer 16 and other portions of the system 10 in greater detail.

A dioxane-containing paste enters the system 10 through a conduit 22 and is pumped to the pre-heater 14 by the pump 12. The paste may contain any desired solids content, and preferably is in a range of about 68 wt. % to about 85 wt. %. The pump 12 meters the paste through the pre-heater 14 where the paste is typically heated to a temperature in a range of 176° F. (80° C.) to about 320° F. (160° C.) (or higher, if necessary) so that the paste is at a selected temperature. The pre-heater 14 may be a heat exchanger wherein heating fluid enters the exchanger through a conduit 25 and exits the exchanger through a conduit 27.

The conduit 22 through which the heated paste travels must be kept under pressure so that no paste components flash in the conduit 22. The restriction to the paste solution flow which maintains the solution under pressure may be supplied by an injection tube 30, and preferably by a plurality of injection tubes 30 through which the paste flows immediately prior to entering the stripper/dryer 16. The injection tube or tubes 30 are designed to supply the required back pressure to prevent flashing in the conduit 22. For example, an injection tube 30 may have an inside diameter ranging from about 0.06 inch to the diameter of a channel of the stripper/dryer 16 to which the injection tube is connected. When a plurality of injection tubes 30 are utilized, the back pressure also insures a uniform distribution of the paste between the tubes.

As the paste moves down the injection tube or tubes 30, the pressure is reduced and components of the paste begin to flash. The vapor liberated during this flashing acts as a motive force to move the increasingly viscous material down into the dryer 16. The pressure of the stripper/dryer 16 is selected by controlling a vent 44 with control means such as a valve 45 so that the desired vaporization occurs.

The paste is introduced into a channel or channels 32 of the stripper/dryer 16 via the injection tube or tubes 30. Each dryer channel is in the form of a conduit, for example a tube 32a, having a flow path (the channel 32) connected to a flow path of an injection tube 30. Each dryer tube 32a preferably has an inside diameter of between about 0.31 inch and 1 inch. Preferably, the stripper/dryer 16 includes a plurality of dryer tubes 32a oriented in a bundle and surrounded by a heat exchange means, such as a jacket 33. Heat transfer material, such as steam, flows into the jacket 33 through a conduit 34 and out of the jacket 33 through a conduit 36.

At an inlet area 38 of the stripper/dryer 16, steam or other vapor or vapor-generating materials may be injected into the stripper/dryer 16 via a conduit 40. As the paste moves down the tube or tubes 32a, heat transferred through the wall of the tube or tubes 32a further vaporizes water and 1,4-dioxane from paste. The velocity of the liquid/vapor paste mixture increases as the vapor is liberated and the pressure drops. The propellent (including the flashing components and steam or other vapor added at 40) and the particles of the detergent paste mix to form the process fluid. Since the process can be operated at various pressures, the gas velocity exiting the dryer tube(s) is typically between about 50 feet/second and about 1500 feet/second. The high process fluid velocities and turbulent flow in the dryer tubes maximize the heat transfer through the walls of the tubes.

As the process fluid leaves the stripper/dryer 16, the dioxane-containing vapor and the purified, concentrated product (e.g., still in paste form) are separated. The vapor is taken through the vent 44 and optionally to a vacuum system (not shown). The purified, concentrated paste is collected in the vessel 18 at the bottom the tube(s) and is removed from the vessel 18 through an outlet conduit 46 utilizing a pump, plodder, extruder or other suitable device 20. In most cases, a pump will be adequate.

From the outlet conduit 46, the purified, concentrated product may be processed in various ways known in the art to produce a final product. As mentioned above, the concentrated paste can be diluted to a concentration corresponding to a local viscosity minimum. Additional components can be added to the paste in the dilution step or additional optional steps.

Figure 3:
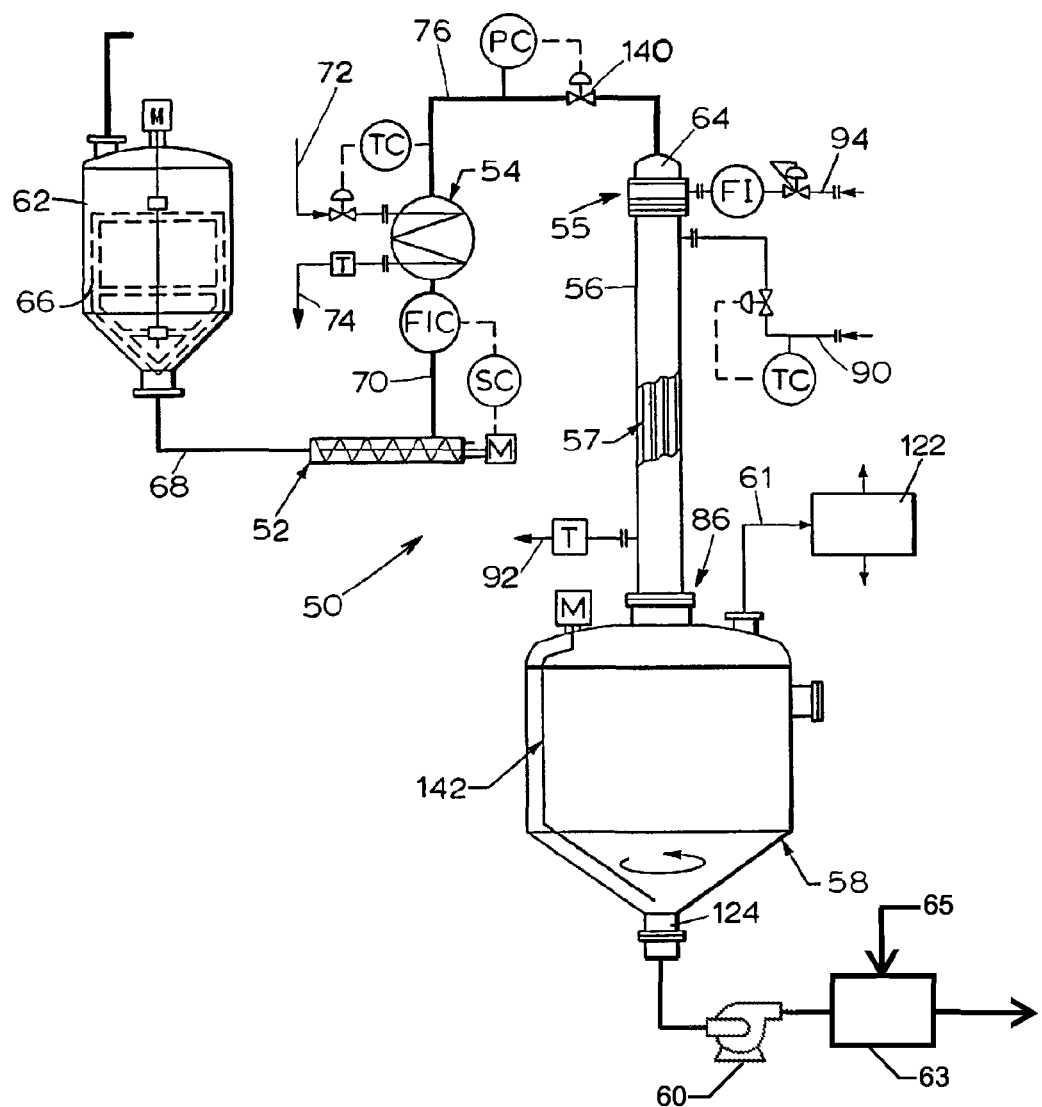
FIG. 3 is a process flow diagram illustrating an embodiment of an apparatus according to the invention.
Figure 4:
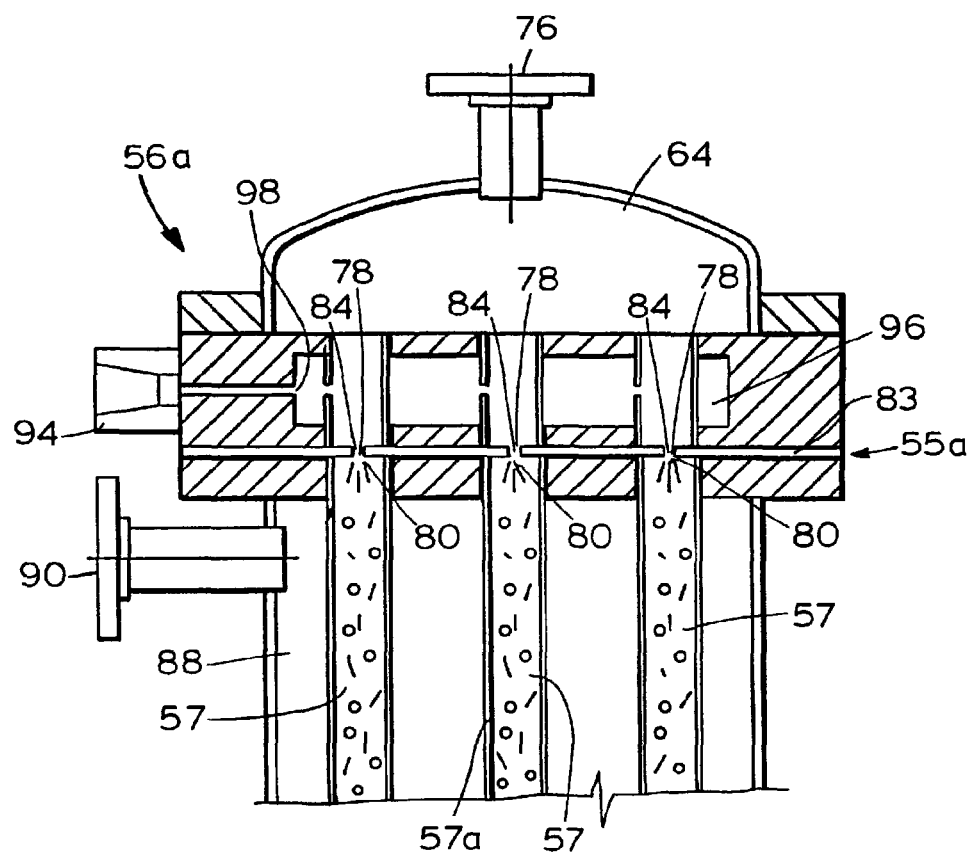
FIG. 4 is a partial, sectional view of a portion of the apparatus shown in FIG. 3.
Figure 5:
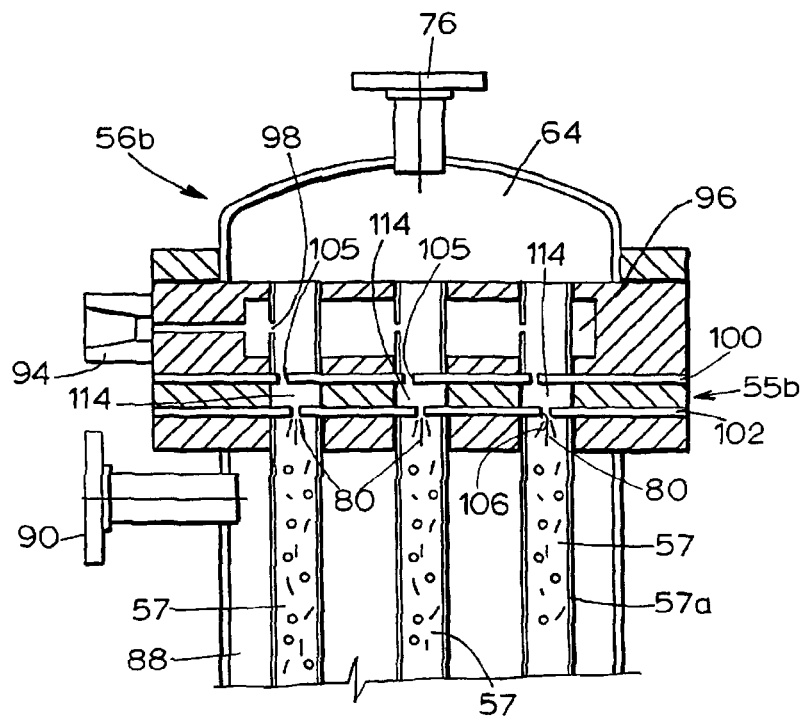
FIG. 5 is a partial, sectional view of a second embodiment of an apparatus according to the invention.

An alternative apparatus and processes are illustrated in drawing FIGS. 3-5. With reference to FIG. 3, an apparatus generally designated 50 includes an inlet pump 52, a pre-heater 54, a restrictive device generally 55, a stripper/dryer 56 having dryer channels defined by tubes 57, a collection vessel 58, an outlet mechanism for the purified, concentrated product, such as a plodder, extruder or pump 60, and a vapor outlet, such as a vent 61. Also shown in FIG. 3 is a feed tank 62 for the supply of a composition into the inlet pump 52.

FIGS. 4 and 5 depict different embodiments of the stripper/dryer 56 shown in FIG. 3 and thus identify the stripper/dryer by the reference numerals 56a and 56b, respectively. However, elements of the stripper/dryer embodiments which are identical will be identified using the same reference numbers. Thus, each of the stripper/dryers 56a and 56b include stripper/dryer tubes 57 disposed downstream of a stripper/dryer inlet or distribution chamber 64. The stripper/dryers 56a and 56b differ with respect to their restrictive devices 55a and 55b, respectively.

The feedstock is fed from the feed tank 62, shown here with an optional wall-wiping agitator 66, by means of the pump 52, through a conduit 68 disposed between the feed tank 62 and the pump 52, and to the pre-heater 54. The pump 52 meters the composition through a conduit 70 and the pre-heater 54.

The pre-heater 54 cam be a standard heat exchanger, such as one having a tube and shell or a plate and frame configuration. Although not limited to any particular design or configuration, the pre-heater 54 is preferably a tubular heat exchanger wherein heating fluid, such as steam, enters the pre-heater 54 through an inlet conduit 72 and exits the pre-heater through an outlet conduit 74, preferably, as a liquid condensate. The heated paste exits the pre-heater 54 through a conduit 76.

The heated composition should be maintained under a pressure sufficient to avoid volatilization of any of the components and to ensure a single-phase flow regime throughout the pre-heater 54, the conduit 76, the inlet/distribution chamber 64, and to the restrictive device 55. Insufficient pressure will result in boiling in the pre-heater 54 and slug-flow in the conduit 76 and inlet/distribution chamber 64. The slug flow will produce uneven flow distribution in the channels 57.

With reference to FIG. 4, to ensure even distribution of the composition into each of the stripper/dryer tubes 57, it is necessary to flow the single-phase composition into the inlet/distribution chamber 64 and through flow restrictions 78 disposed between the inlet/distribution chamber 64 and the stripper/dryer tubes 57, immediately upstream of inlets 80 to each dryer tube 57. Each flow restriction 78 defines a passage between the inlet/distribution chamber 64 and the dryer tube 57 which is smaller in cross-section than a diameter of the stripper/dryer tube 57 at its inlet 80. The flow restriction may be formed by, for example, a small tube, a nozzle, or an aperture, such as a bore hole extending through a plate, with the cross-sectional area of the void defined by the tube, nozzle or bore being smaller than the cross-sectional area of the channel defined by the stripper/dryer tube 57 (or other geometry forming the channel). In the embodiment shown in FIG. 4, the device 55a which provides for all of the restrictions 78 is an orifice plate 83 disposed between the inlet/distribution chamber 64 and each of the dryer tubes 57. The plate 83 includes a plurality of bore holes 84, the substantially cylindrical wall defining each bore hole 84 forming each flow restriction 78. The flow restriction 78 diameter preferably ranges between about 0.75 millimeters (mm) (0.03 inches) and about 2 mm (0.08 inches). The stripper/dryer tube 57 diameter can be in range of about 6.35 mm (0.25 inches) to about 25.4 mm (1 inch), for example. As the composition flows through the restrictions 78, the pressure reduces, allowing a portion of the water and dioxane to vaporize, increasing the vapor velocity, thus promoting two-phase flow. The sizable pressure drop produced by flashing water is the reason that the upstream paste flow remains as a single-phase flow with no boiling and vaporizing in the pre-heater 54, conduit 76 and inlet/distribution chamber 64. The vaporization of a portion of the water as it passes through the flow restrictions 78 contributes indirectly to the flow distribution to each channel 57 by creating the vapor velocity necessary for two-phase flow. The low pressure drop across the channels 57 in the two-phase flow regime enables and promotes substantially uniform flow distribution to each channel 57.

To explain this further, if we designate P1 as the pressure in the inlet/distribution chamber 64, P2 the pressure at the inlet of each channel 57, and P3 the pressure in the product receiver tank 58, then the inlet pressure P1 to all flow restrictions 78 will be the same because of the common inlet/distribution chamber 64. Also, the outlet pressure of all channels will be the same P3 because of the common receiver tank 58. However, the pressure P2 at the inlet 80 to each channel 57 will be constant only if the pressure drop through each channel 57, P2-P3, is constant. This is achieved only with two-phase flow throughout the all of the plurality of channels 57. If P1, P2, and P3 are the same for each drying channel, then the known fluid mechanic equations describing such flow regimes state that the flow rate will be constant in each channel 57.

If uneven amounts of paste are passed to the channels 57, such uneven distribution causes inadequate and/or uneven stripping/drying within the channels 57 and causes the channels 57 to become plugged. Channel plugging itself contributes to further uneven and/or inadequate stripping/drying of the paste. This is why good flow distribution is so important in a multi-channel stripper/dryer.

The composition leaving the restriction 78 passes in two-phase flow through heated channels 57 where water will vaporize and strip out additional dioxane, and thereby force the increasingly viscous composition through outlets 86 of the channels 57 and into the collection vessel 58. Preferably the channels 57 are tubes oriented in a bundle within the stripper/dryer 56, and are surrounded by a common heat transfer mechanism, such as a shared jacket 88 in which steam can be introduced. Heat transfer fluid, such as steam, flows into the jacket 88 through a conduit 90, and steam and/or condensate flows out of the jacket through a conduit 92. The length, internal diameter, thickness, and material of construction of the channels 57 are selected to achieve adequate stripping of dioxane. For example, in one embodiment each channel or tube 57 has an inside diameter of about 6.35 mm (0.25 inch) to about 25.4 mm (1 inch), for example 1 cm (0.4 inch). Each tube can have a length of about 2 meters to 6 meters, for example, preferably about 3 meters. However, it is noted that other embodiments of the invention may employ channels or conduits having equivalent diameters as defined in Table 5-8 of Perry's Chemical Engineers' Handbook, 5-25 (6th ed. 1984) (see also, 7th ed. 1997 at 6-12 to 6-13). Furthermore, the channels, tubes, or conduits may be tapered to ensure a gradual increase in gas velocity as the composition becomes drier.

It is believed that uniform distribution of composition through the stripper/dryer tubes 57 is aided by the use of the heat jacket 88. For example, if a tube 57 begins to clog, there will be a reduced flow of composition into that tube. This in turn reduces the pressure drop across the bore hole 84 through which the composition is fed into the tube 57 and increases the pressure drop within the tube 57. Because the walls of the tube 57 are heated at a substantially constant rate, pressure will increase at the entrance of the clogged tube 57 until vapor pressure upstream of the clog is sufficient to blow the tube 57 clear and re-establish two-phase flow at the tube inlet 80.

The motive force for driving the composition through the entire length of the drying channel 57 is dependent on the velocity of vapor in the drying channel 57. If the vapor velocity is too low, it will not sustain the desired two-phase flow. As stated above, minimum velocities are somewhat dependent upon the physical properties of the composition, such as viscosity. However, in general, the mass flow rate of vapor should be above 39,000 kg/hr/m$^2$ (8000 lbs/hr/ft$^2$) of drying channel cross-sectional area.

Steam and/or other types of vapor means may be introduced into the inlet/distribution chamber 64 via a conduit 94 into a common steam header 96 and then into each channel inlet 80 through a flow restriction 98. Where sufficient flashing occurs within the channels 57 to reduce dioxane, however, simultaneous steam injection may be unnecessary.

As discussed above, FIG. 4 shows an embodiment wherein the flow restriction device 55a is the orifice plate 83 located at the channel 57 entrance with bore holes 84 drilled at the entrance to each channel 57. Somewhat better temperature-pressure equilibrium can be achieved in some applications by using the restriction device 55b shown in FIG. 5 which includes two orifice plates 100 and 102. The orifice plates 100 and 102 provide for a plurality of flow restrictions arranged in series upstream of each tube 57. Specifically, with reference to FIG. 5a, a first restriction 105 and a second restriction 106 are disposed in series separated from each other by a gasket 108. Each flow restriction 105, 106 and the gasket 108 defines a bore hole. Each bore hole 109 of the first flow restriction 105 is in fluid communication with at least one bore hole 110 of the gasket 108 and a bore hole 112 of the second restriction 106, and at least one tube 57. In order to provide a flow restriction, the diameter of each bore hole 109 and 112 is smaller than the inner diameter of the tubes 57. Preferably, and as shown in FIG. 5, the bore holes 109 and 112 also are smaller than the diameter of the gasket bore hole 110. Exemplary diameters of the restriction bore holes 109, 112, the gasket bore hole 110 and the inner diameter of the tube 57 are 1.6 mm (0.0625 inches), 12.7 mm (0.5 inches), and 12.7 mm (0.5 inches), respectively. Based on the relative diameter sizes a chamber 114 is disposed between each two restrictions 105, 106. The top and bottom portions of the chamber 114 are defined by the first and second restrictions 105 and 106, respectively, and sidewalls 116 of the chamber 114 are defined by the thickness of the gasket 108.

Figure 5A:
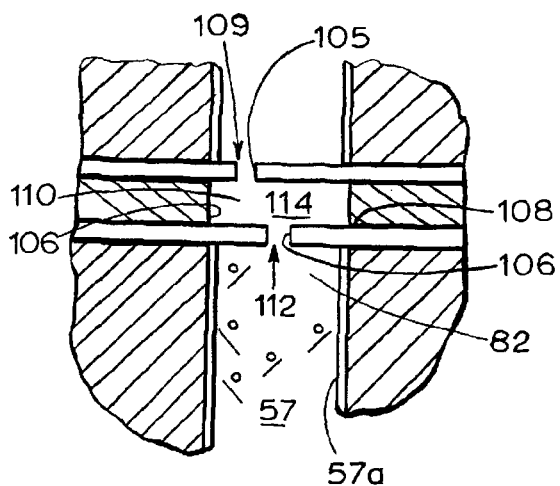
FIG. 5A is an enlarged view of a portion of the embodiment of the apparatus shown in FIG. 5.

As shown in FIGS. 5 and 5A, the restrictions 105, 106, and the bore holes 109, 112 therein are not aligned with each other; but instead, have center axes that are staggered about 3 mm (0.125 inches) off of the centerline. Thus, the flow of the composition through the restrictions 105 and 106 is "snake-like" and not a straight line. This is believed to help in providing a sufficient back-pressure in the upstream conduit 76 and the pre-heater 54. As the heated, single-phase composition passes into and through the first restriction 105, a two-phase flow exits into the chamber 114. As the two-phase flow exits the chamber 114 and passes into the second restriction 106, more water vapor is flashed and a more voluminous two-phase flow exits into the inlets 80 of the tubes 57. The onset of the two-phase flow phenomena is the same as that detailed above with respect to the single restriction dryer design shown in FIG. 4 and similarly provides for sufficient back pressure and sufficient pressure drop to generate maximum flash, and even distribution of flow throughout the multiple channels 57.

Sufficient back pressure is achieved since the flow of paste is greatly restricted as it enters and passes through the flow restriction device 55b. A sufficient pressure drop through the flow-restriction devices 55a and 55b is due in large part to what is known as "velocity head" pressure loss. Prior to entering a flow restriction, a paste may be in the form of a single-phase liquid-gel. As the single-phase paste passes through the flow restriction 78 or flow restrictions 105 and 106, part of the paste volatilizes to a foam-like, two-phase material due to a pressure drop (for example, about 3 bar (45 pounds per square inch (psi)) to about 15 bar (225 psi)) experienced as the material flows through the restriction. The rapid increase in velocity results in the "velocity head" pressure loss—the pressure loss necessary for maximizing vaporization of water from the paste. A sufficient velocity head pressure loss may be attainable in most instances simply by using a single orifice plate 83 as shown in FIG. 4 instead of dual orifice plates 100 and 102 shown in FIG. 5. As mentioned above, other suitable restrictive devices include convergent nozzles, divergent nozzles, convergent and divergent nozzles, small diameter injector tubes and other shapes that can be manufactured with identical flow geometry. The orifice size in all of these devices must be small enough to produce sufficient two-phase flow velocity for the required back pressure and will also depend on the desired flow-rate to each orifice.

Even flow through each channel 57 is ensured by keeping the pressure drop constant across each channel 57. In this way, the flow restrictions 105 and 106 are evenly distributing the flow to a point of even pressure in each stripping/drying channel inlet. The constant pressure drop in each channel 57 can only be maintained if two-phase flow exists across the entire length of the channel 57. The combination of the pre-heater 54 and flow restrictions 78 (or 105 and 106) work together to indirectly produce the desired uniform flow distribution. It is noted that traditional flashing of a material through an orifice will only distribute flow evenly if it is flashing to a common chamber at constant pressure, which is not the case in this apparatus and method. The drying channels 57 lie between the flow restriction and the common receiver vessel 58. Therefore, achieving conditions for two-phase flow regime in all drying channels in combination with a common chamber at the end of each channel 57, enables essentially constant inlet pressure at the inlet of each channel 57 and therefore the distribution is uniform.

Once a flow restriction 78 (or 105 and 106) is installed, it does not need to be replaced each time a different back pressure is desired. The amount of back pressure generated by the installed restriction can be adjusted by varying certain operating conditions throughout the process. For example, the variables governing the pressure drop across a given flow restriction include both the flow rate and temperature of the feed composition. To achieve the relatively high pressure drop required to prevent flashing in the pre-heater 54, the cross-sectional area of the orifice in the restriction must be small enough so that when the liquid flashes to two phases, the vapor velocity is high enough to result in the desired pressure drop. The higher the temperature of the feed composition, the higher vapor velocity and, thus, the higher the pressure drop across the flow-restriction. Recall, that the temperature of the feed composition is controlled by the upstream pre-heater 54. If the composition is not superheated in the preheater 54, no flashing will occur in the flow restriction and the pressure drop will be relatively low.

As the composition flows through the flow restriction 78 (or 105 and 106), the pressure is reduced and the water and dioxane components flash to vapor phase. The vapor liberated during this flashing acts as a motive force to propel the remainder of the composition through the dryer tubes 57. The water vapor liberated serves to strip dioxane from the composition. The absolute pressure within the channels 57 of the stripper/dryer is selected by controlling, among other things, a vent 61 of the stripper/dryer 56 so that a desired vaporization occurs. The pressure drop across the channels 57 when operating in two phase flow can be relatively low in most cases, for example in a range of about 0.5 bar (7.5 psi) to 2.0 bar (30 psi).

As the remainder of the composition passes through the channels 57, heat transferred through the walls 57a of the tubes 57 vaporizes additional water from the composition. The velocity of the two-phase liquid/vapor mixture increases as the vapor is liberated and as the pressure drops. The propellent (including the flashing solvents and steam or other propellent that may be added via the conduit 94) and the particles of the composition mix to form two-phase flow. Since the process can be operated at various pressures under vacuum by controlling the flow of the vapor through the vent 61, the gas velocity exiting the channels 57 can be maintained in a range of about 15.25 meters per second (m/sec) (50 feet per second (ft/sec)) to about 460 m/sec (1,500 ft/sec), for example. High two-phase flow velocity and turbulent flow in the dryer channels 57 maximize the heat transfer through the walls 57a of the channels 57.

The temperature at the restriction inlet is used to control the amount of flash. The temperature of the restriction inlet, therefore, should be high enough to generate vapor flashing sufficient to strip dioxane from the composition and propel the paste through the restriction and channel into the receiver tank without plugging the channel. Inlet temperatures and their relationship to the amount of flash generated are dependent, of course, on the particular composition and, the heat sensitivity of the composition. The dryness of the product is controlled primarily by the temperature of the heating fluid in the dryer jacket 88. This temperature may also be limited by the heat sensitivity of the product. Hence each different composition may require a different set of operating conditions.

As the two-phase flow exits the stripper/dryer 56, the dioxane-containing vapor and purified, concentrated composition are separated. The dioxane-containing vapor is passed through the vent 61 and, optionally, to a vacuum system 122. The purified, concentrated composition is collected in the vessel 58 located at the exit of the channels and is removed from the vessel 58 through an outlet conduit 124 utilizing a pump, plodder, extruder or other device 60 and diluted in diluter 63 with process water 65. The vessel 58 operates at a pressure less than an operating pressure of the channel outlets, and under vacuum. Operating the vessel 58 under such reduced pressure and/or vacuum conditions enables easy separation of vapor and purified, concentrated material.

From the outlet conduit 124, the purified, concentrated product may be subjected to various unit operations known in the art in order to produce a final product. In many cases, the hot product discharged from the stripper/dryer 56 is cooled before storage or dilution.

The purified, concentrated product may also be diluted, as described herein.

The drying processes and apparatus may be used to form purified, concentrated detergent from feed materials having a wide range of viscosities and dioxane contents. For example, a heated material fed to the dryer 56 may range from a thin paste (approximately 50 centipoise) to a very thick paste (approximately 500,000 centipoise).

Figure 18:
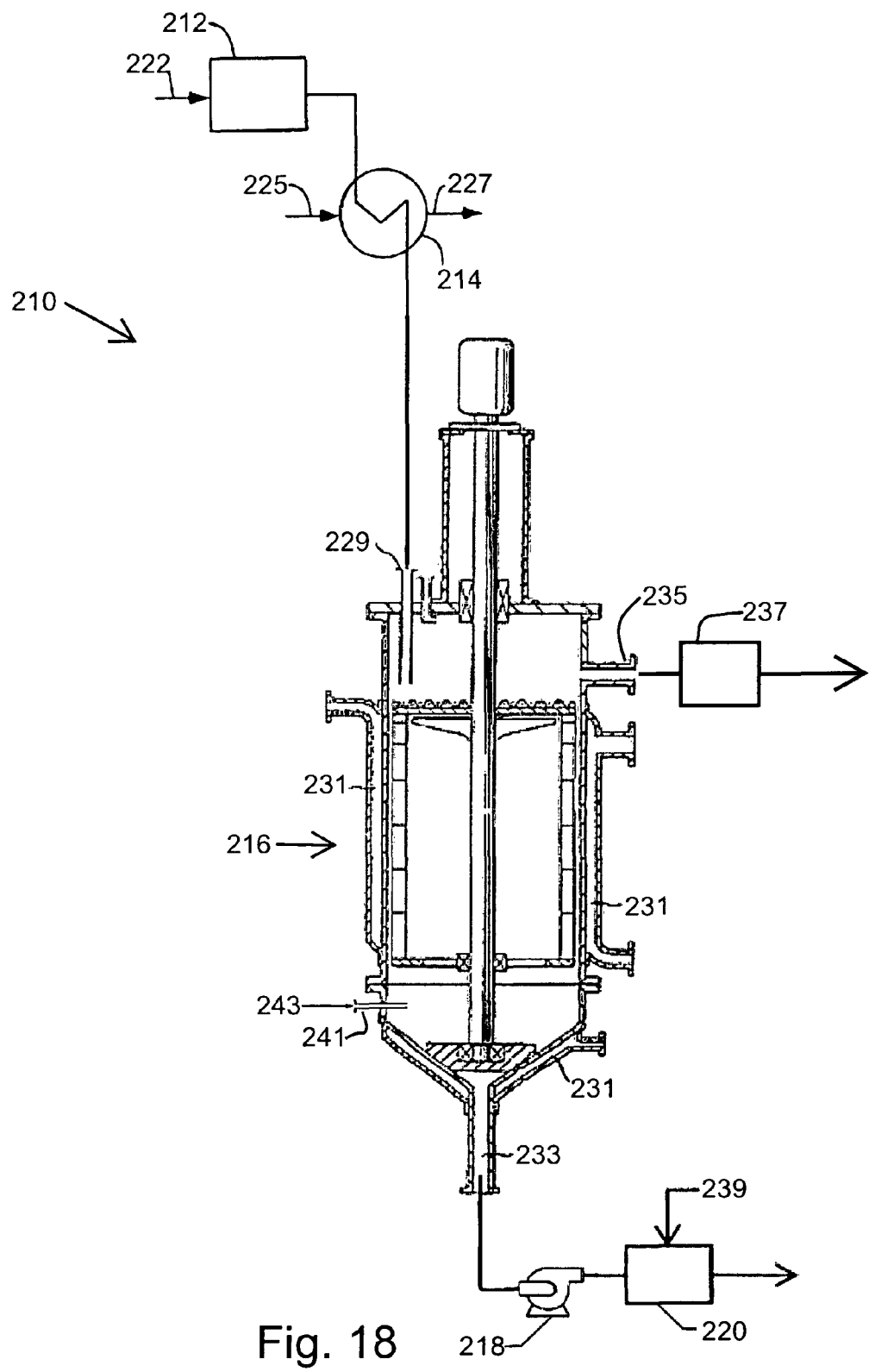
FIG. 18 is a process flow diagram illustrating a solvent removal system for use in the process according to the invention employing a wiped film evaporator.

Another process and apparatus according to the invention is further illustrated in FIG. 18 in which the dioxane removal system generally designated 210 comprises an inlet pump 212, an optional pre-heater 214, a wiped film evaporator 216, an outlet means such as a plodder, extruder or pump 218, and a diluter 220. In most cases, a pump will be adequate.

A dioxane-containing paste enters the system 10 through a conduit 222 and is pumped to the optional pre-heater 214 by the pump 212. The paste may contain any desired solids content, and preferably is in a range of about 68 wt. % to about 85 wt. %. The pump 212 meters the paste through the pre-heater 214 where the paste is typically heated to a temperature in a range of 176° F. (80° C.) to about 320° F. (160° C.) (or higher, if necessary) so that the paste is at a selected temperature. The pre-heater 214 may be a heat exchanger wherein heating fluid enters the exchanger through a conduit 225 and exits the exchanger through a conduit 227.

The conduit 222 through which the heated paste travels must be kept under pressure so that no paste components flash in the conduit 222. The paste is introduced to the wiped film evaporator 216 via inlet 229. The evaporator 216 is jacketed for heating (elements 231). The paste moves down the evaporator to outlet 233. The dioxane-containing vapor stream exits through gas outlet 235, which is in communication with vacuum pump 237. As the paste moves down evaporator 216, heat transferred through the wall of the evaporator 216 from the heating jacket 231 further vaporizes water and dioxane from paste.

As the process fluid leaves the evaporator 216, the dioxane-containing vapor and the purified, concentrated product (e.g., still in paste form) are separated. The vapor is taken through the vent 235 and optionally to a vacuum system 237. The purified, concentrated paste is collected in the evaporator 216 at the bottom and is removed from the evaporator 216 through an outlet conduit 233 utilizing a pump, plodder, extruder or other suitable device 218. In most cases, a pump will be adequate. The purified paste is diluted in diluter 220 with process water 239. The system 210 can optionally include an inlet 241 towards the bottom of the evaporator 216, e.g. for injection of steam 243 or another gas.

Theory

Following is the nomenclature used in this theoretical section:

$ppm_X$ is always parts per million of dioxane in stream X
$\%_X$ is always percent water in stream X
$\% A_X$ is percent active in stream X
$M_X$ is mole flow rate of X
$Mw_X$ is molecular weight of X
$\#_x$ is mass or weight flow rate of X
$x_x$ is the mole fraction of X in the liquid state
$y_x$ is the mole fraction of X in the vapor state
$V_{p\ X}^{0}$ is the Vapor Pressure of component X
$P_T$ is the total pressure of the system where equilibrium occurs Values of X
D is dioxane
W is water
Air is air
V is vapor
P is product
F is feed
S is steam
i is any component used consistently throughout an equation Constants and ratios will be defined as used.

Dioxane reduction ratio, $D_R$, is defined as the ratio of the dioxane of the feed divided by the dioxane level of the product. This assumes that the water content of the product is the same as the feed, which is not always true. The correct definition is:

$$D_R \equiv \frac{ppm_F/\% A_F}{ppm_P/\% A_F} \quad \text{Equation 1}$$

Starting from the above definition, Equation 1, we can derive an expression for dioxane reduction ratio in terms that can be used to predict the performance of a system.

The following is the dioxane balance around the system:

$$\#_F ppm_F = \#_P ppm_P + \#_V ppm_V$$

Next is the active balance around the system:

$$\#_F \% A_F = \#_P \% A_P$$

Combine the equations and we get:

$$\frac{\#_F ppm_F}{\#_F \% A_F} = \frac{\#_P ppm_P + \#_V ppm_V}{\#_P \% A_P}$$

Which simplifies to:

$$\frac{ppm_F}{\% A_F} = \frac{ppm_P + \#_V/\#_P ppm_V}{\% A_P}$$

The left side of the simplified combined equation is identical to the top term used in the definition of the dioxane reduction ratio so we can substitute into Equation 1:

$$D_R = \frac{\frac{ppm_P + \#_V/\#_P ppm_V}{\% A_P}}{ppm_P/\% A_P}$$

Which in turn simplifies to:

$$D_R = 1 + \#_V/\#_P ppm_V/ppm_P \quad \text{Equation 2}$$

The term Steam Ratio $S_R$ is used to describe the amount of stripping steam used in the process. The Steam Ratio is equal to the amount of steam in equilibrium with the final product or:

$$S_R = \#_S/\#_P = \#_V/\#_P$$

Since the vapor in the system is essentially pure water, the few parts per million dioxane can safely be ignored we can modify the equation for dioxane reduction ratio to:

$$D_R = 1 + S_R ppm_V/ppm_P \quad \text{Equation 3}$$

This equation is very useful in that the steam ratio is a variable controlled by the operator and the dioxane content of the product is the variable which we are trying to attain. To predict the dioxane ratio, the dioxane content of the vapor phase has to be determined using variables that would be controlled by the operator.

When evaluating a system it is essential to determine the vapor/liquid equilibrium which is the maximum separation possible in one stage. The three following analyses treat the system as an ideal binary system, then a binary system with empirical data and finally as a non-binary system using a non-condensable gas for stripping.

Ideal Solution

The theoretical equilibrium can be determined from Raoult's Law and Dalton's Law which relate the partial pressure of a component to the mole fraction of that component in the liquid and vapor phases as follows:

$$x_i V^0_{P_i} = p_i = y_i P_T$$

The partial pressure can be eliminated yielding the following equation:

$$P_T = \frac{x_i}{y_i} V^0_{P_i}$$

The system's total pressure can be used to determine the relationship of any two components and in the case of interest to us:

$$\frac{x_D}{y_D} V^0_{P_D} = \frac{x_W}{y_W} V^0_{P_W}$$

$$y_D = y_W \frac{x_D}{x_W} V^0_{P_D} / V^0_{P_W}$$

Note that the same type of relationship could be developed for any compound in the active. As an example, oil has a significant vapor pressure and experience shows that the oil content is reduced when stripping.

In separation processes, the Separation Factor is commonly used to simplify the equation which, in the case of vapor equilibrium, is the ratio of the vapor pressure of the two components at the equilibrium temperature (relative volatility). A graph of the separation factor for dioxane and water verses temperature follows the development of the equation. The separation factor is defined as:

$$\frac{V^0_{P_D}}{V^0_{P_W}} = S_f$$

The equation becomes:

$$y_D = y_W \frac{x_D}{x_W} S_f \quad \text{Equation 4}$$

Figure 6:
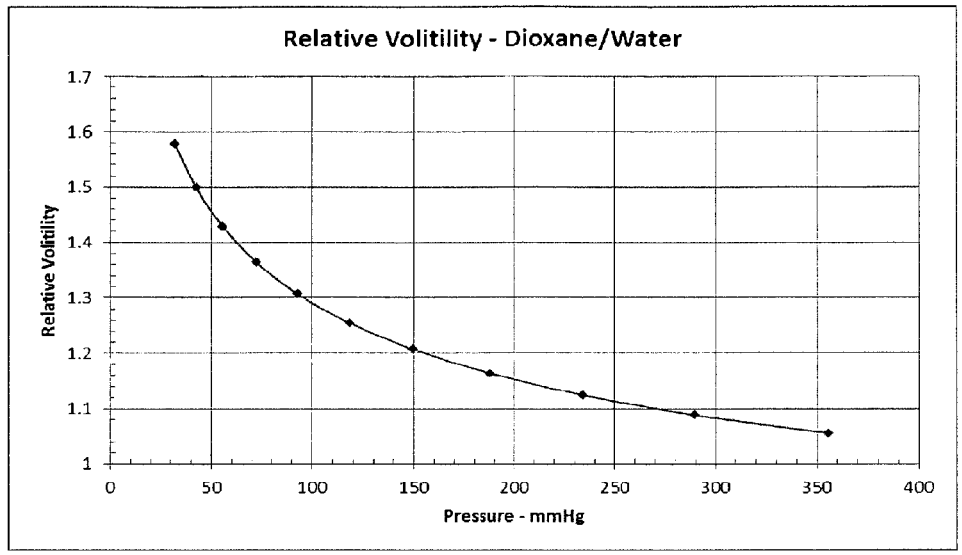
FIG. 6 is a graph of separation factor (Relative Volatility) as a function of pressure.
Figure 7:
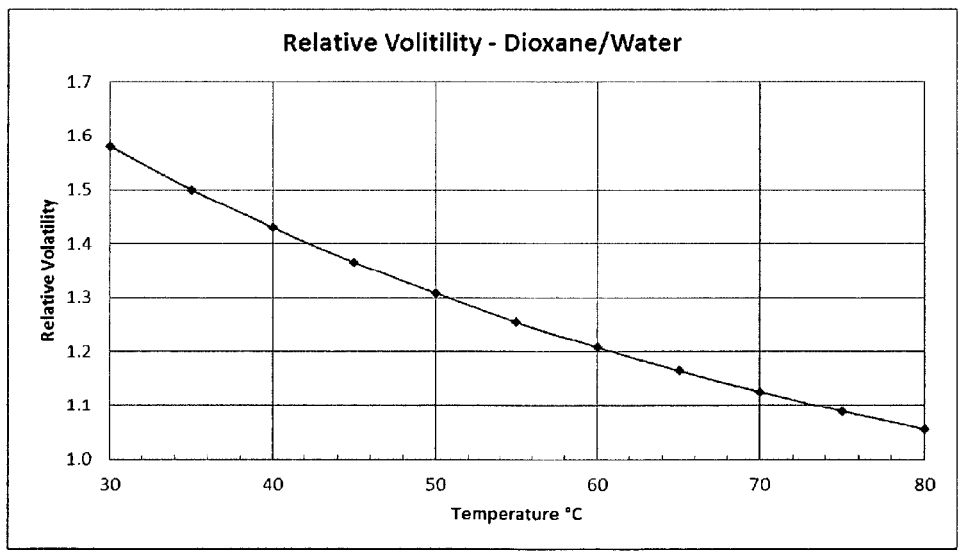
FIG. 7 is a graph of separation factor (Relative Volatility) as a function of temperature.

Graphs of the separation factor (Relative Volatility) is shown with two different x axes in FIG. 6 and FIG. 7. Since the vapor phase is almost pure water, the temperature of steam at a pressure can be used to equate the axes, but in both cases the temperature and the pressure should be measured in the flash vessel and the temperature should be of the paste in specific. We are trying to determine the equilibrium; therefore properties of the paste and vapor at the inlet of the stripper are not of interest since they are not at equilibrium but must be measured at the flash tank, the last place the paste and vapor are in contact before separation.

The equation can be further modified to use variables that are commonly determined and available in the real world.

$$y_D = ppm_V \#_V Mw_D/M_C/1{,}000{,}000$$

$$y_w = \%_V \#_V Mw_W/M_V/100\%$$

$$x_D = ppm_P \#_P Mw_D/M_P/1{,}000{,}000$$

$$x_w = \%_P \#_P Mw_W/M_P/100\%$$

Substituting into Equation 4:

$$ppm_T \#_T/Mw_D/M_T/1{,}000{,}000 = (\%_T\#_T/Mw_W/M_T/100\%)$$
$$(ppm_P\#_P/Mw_D/M_P/1{,}000{,}000)/(\%_P\#_P/Mw_W/M_P/100\%)S_f$$

The simplified equation is:

$$ppm_T/ppm_P = S_f(\%_T/\%_P):\qquad\text{Equation 5}$$

This equation makes no assumptions about the composition of the two streams and it gives us the term we needed in Equation 2 to make a theoretical determination of the dioxane reduction.

$$D_R = 1 + S_R ppm_T/ppm_P \qquad\text{Equation 3}$$

Substituting Equation 5 into equation 3 we get:

$$D_R = 1 + S_R S_f \%_T/\%_P \qquad\text{Equation 6}$$

By setting $(S_f\%_T/\%_P)$ to equal $I_f$, the equation is simplified to:

$$D_R = 1 + S_R I_f \qquad\text{Equation 7}$$

Figure 8:
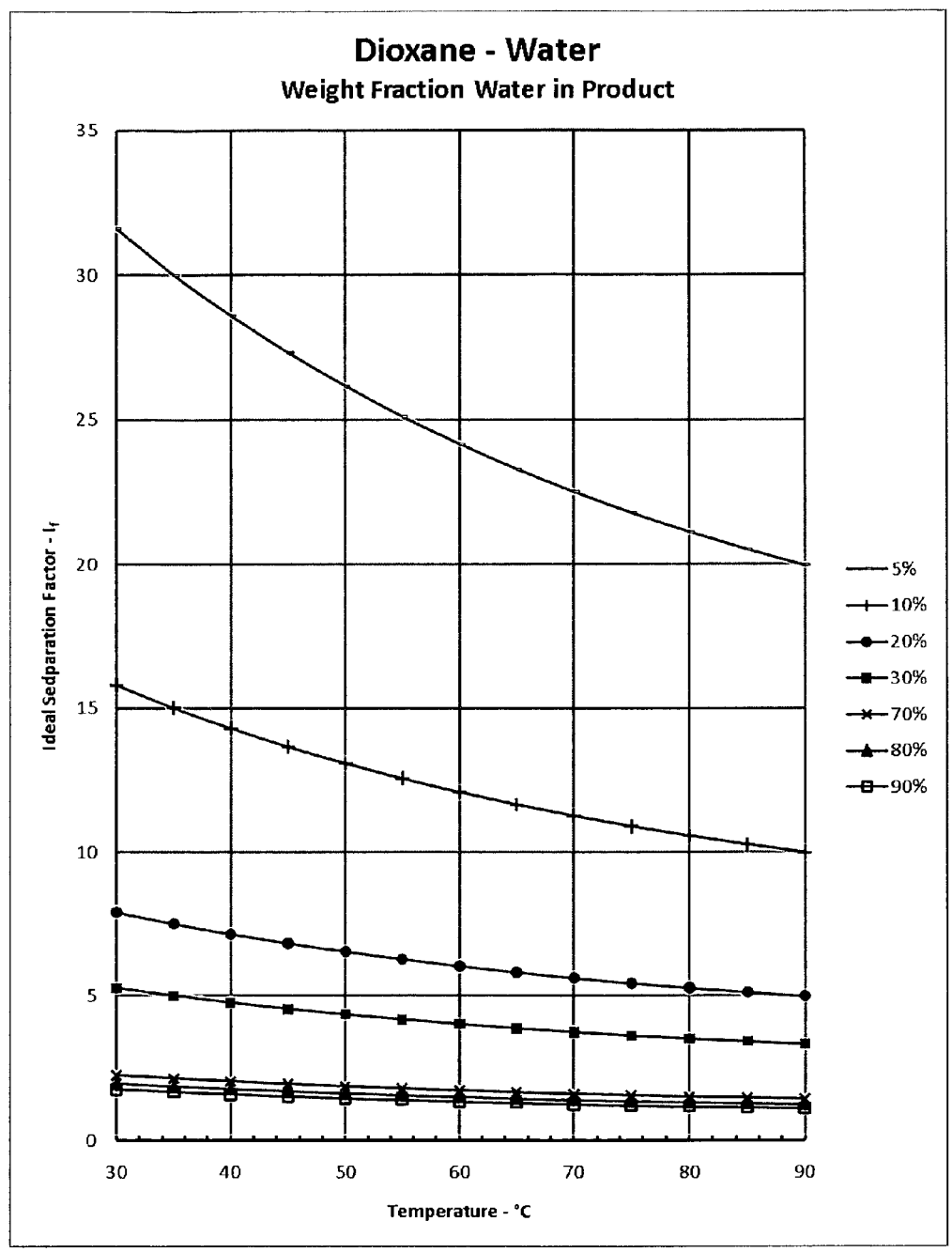
FIG. 8 shows values of ideal separation factor ($I_f$) at different concentrations.
Figure 9:
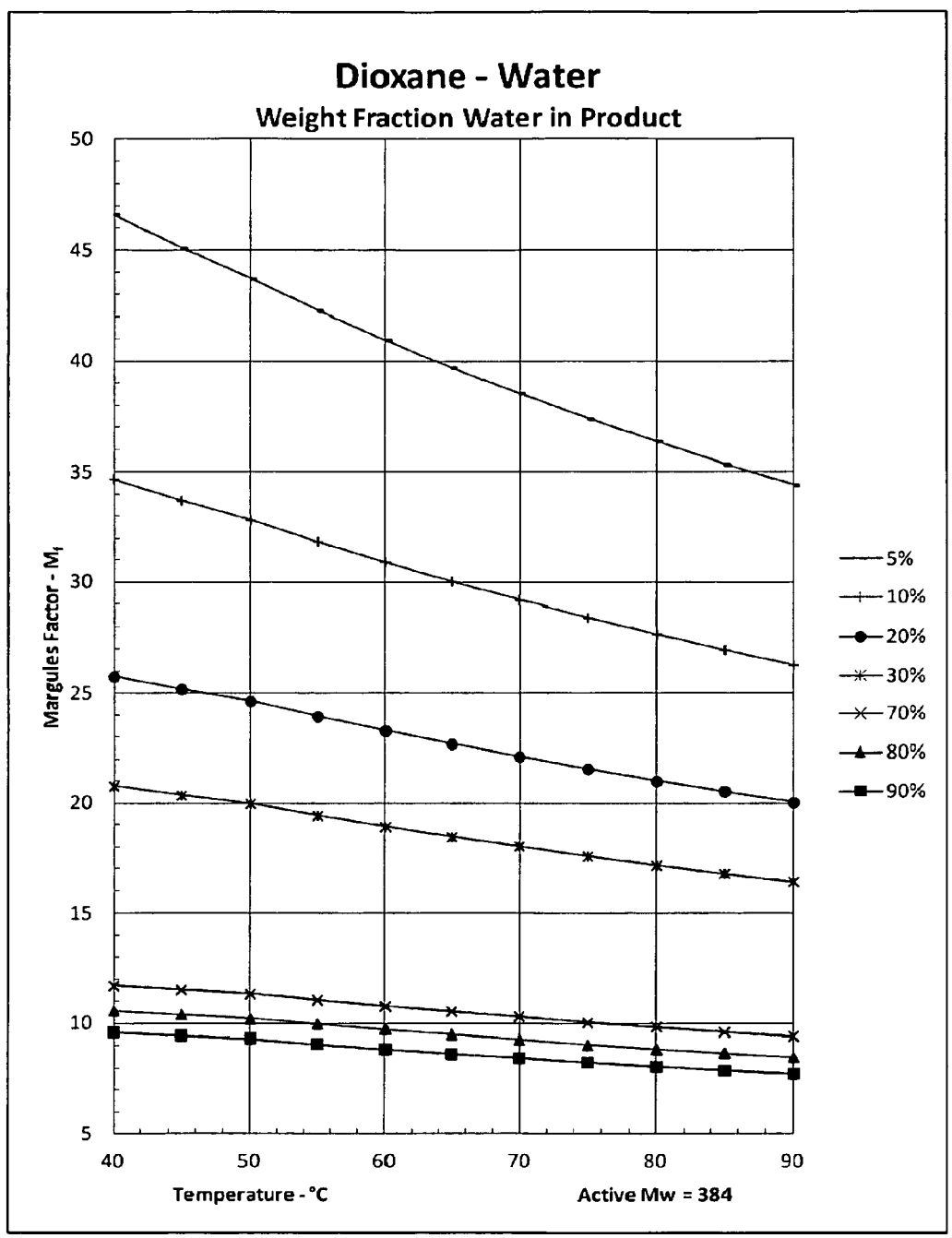
FIGS. 9-16 show the Margules factor for different active concentrations with various active molecular weights. The graphs are duplicated with the first group showing the Margules factor verses temperature of the active and the seconds set verses the flash tank pressure.
Figure 10:
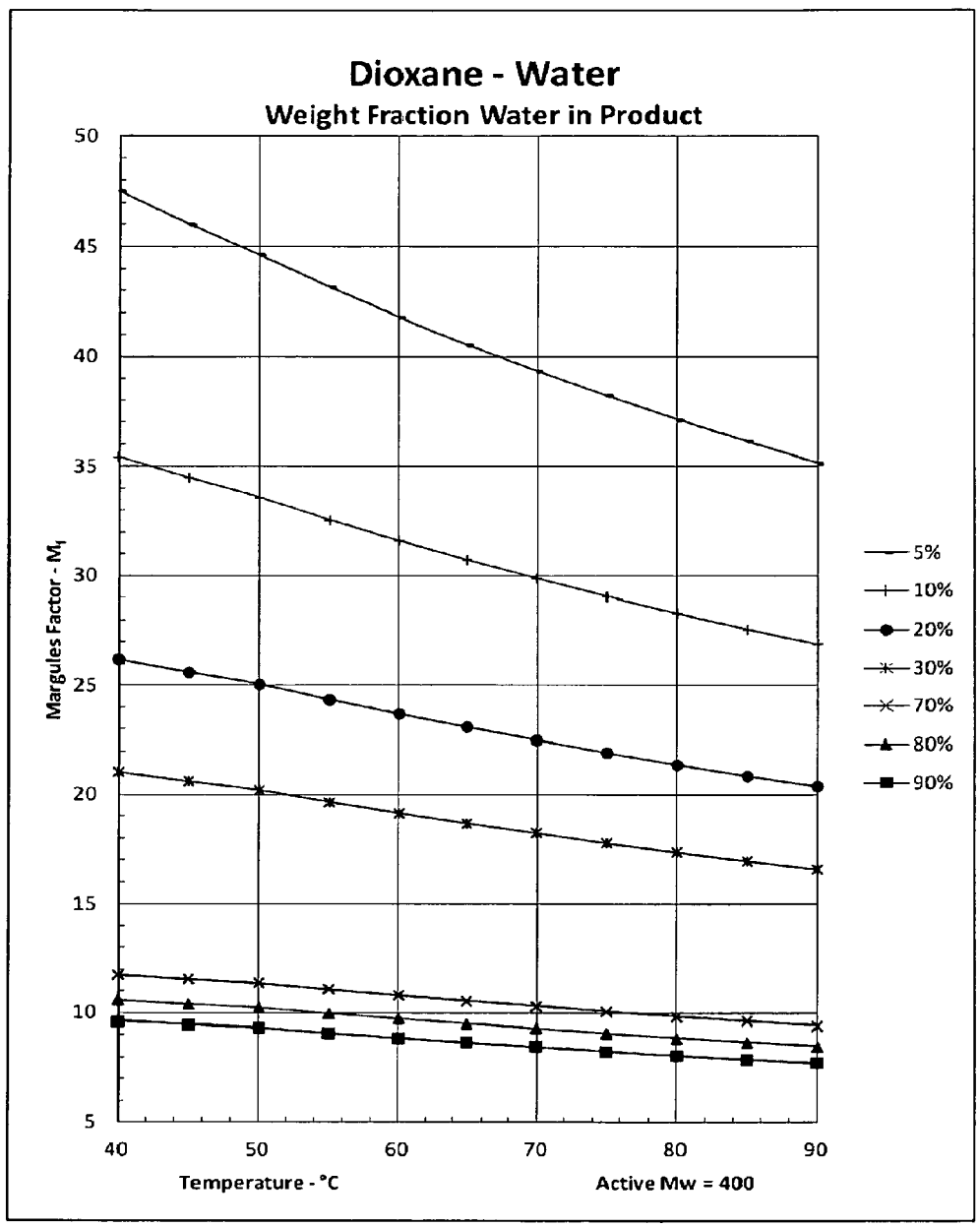
Figure 11:
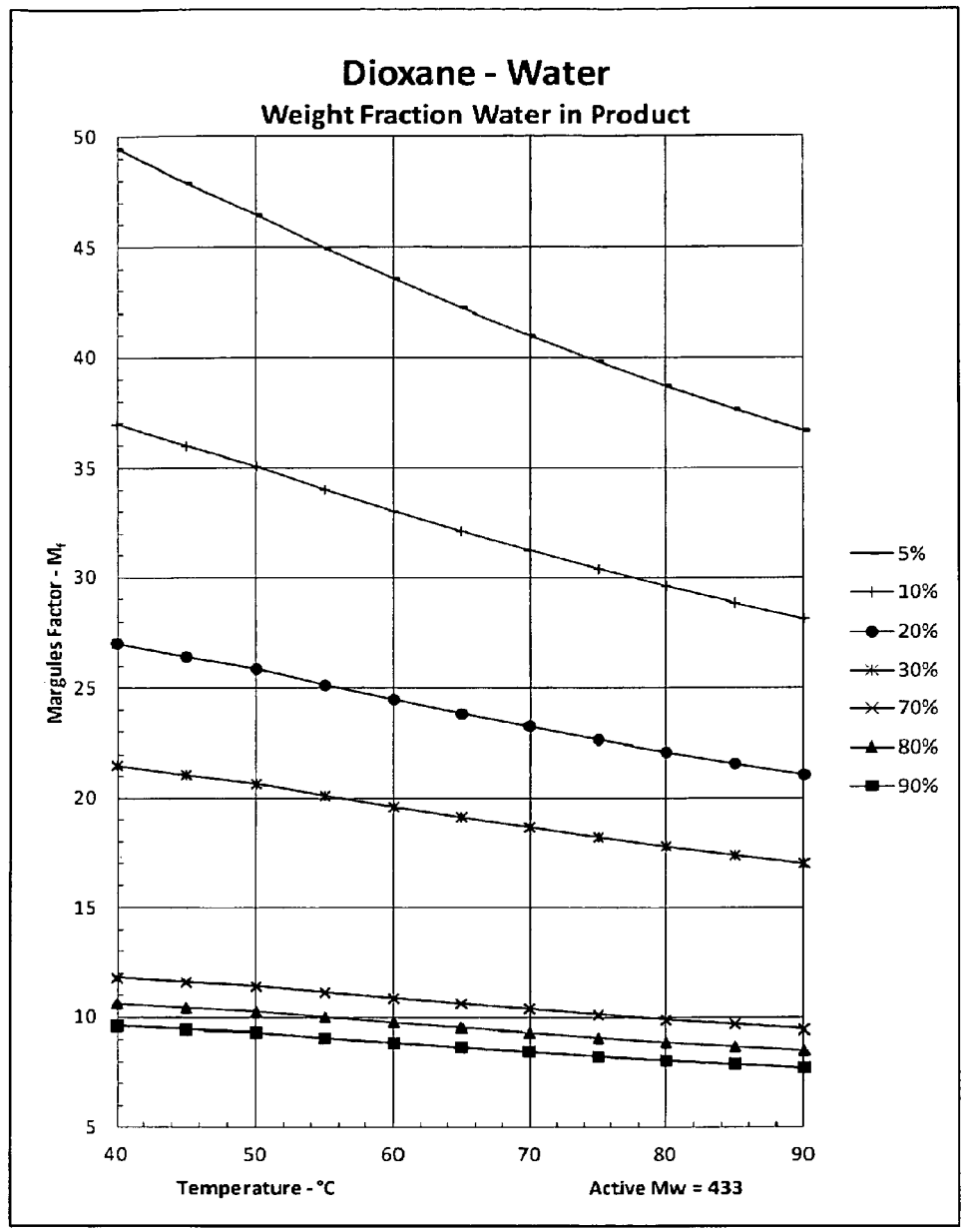
Figure 12:
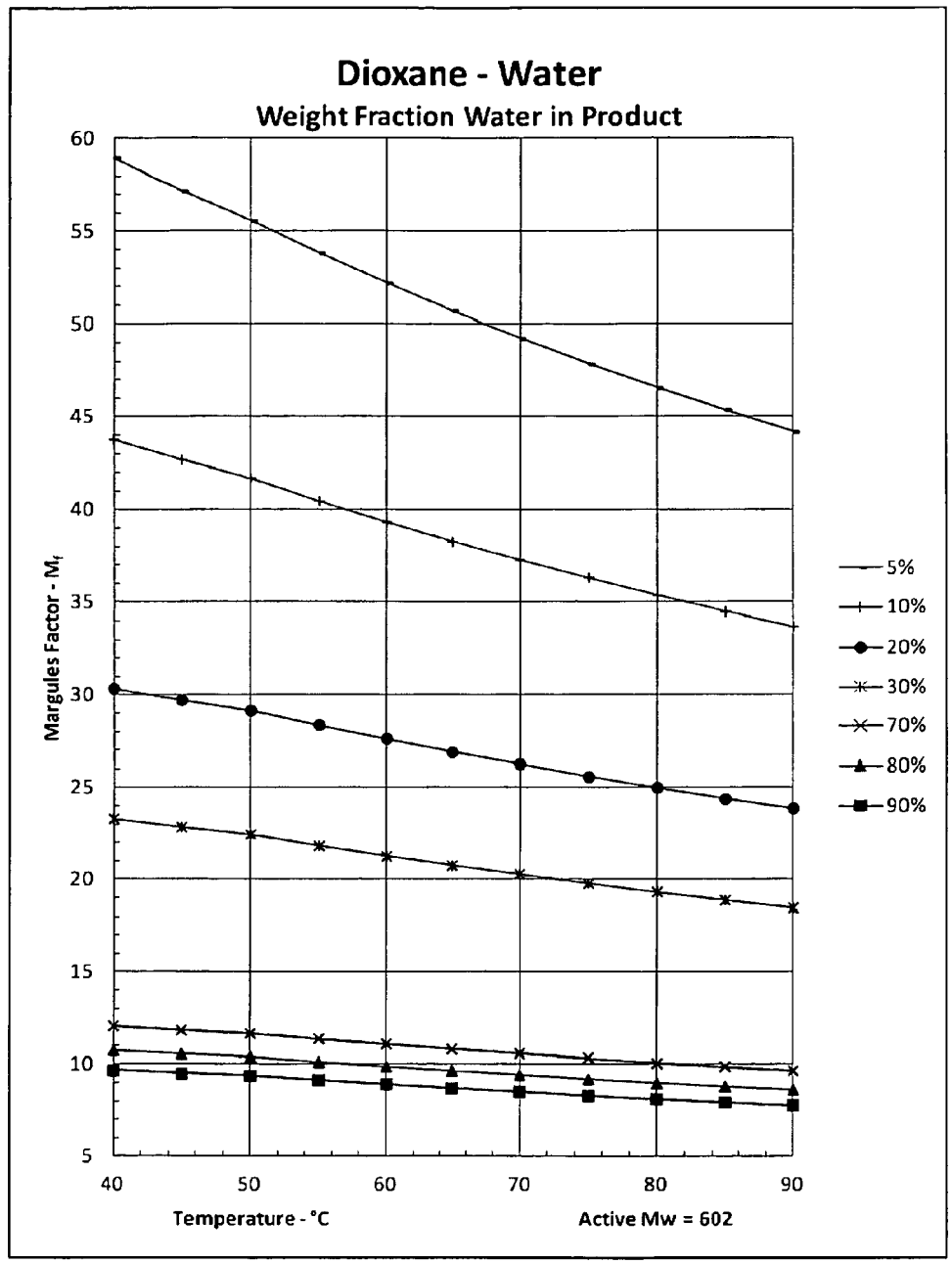
Figure 13:
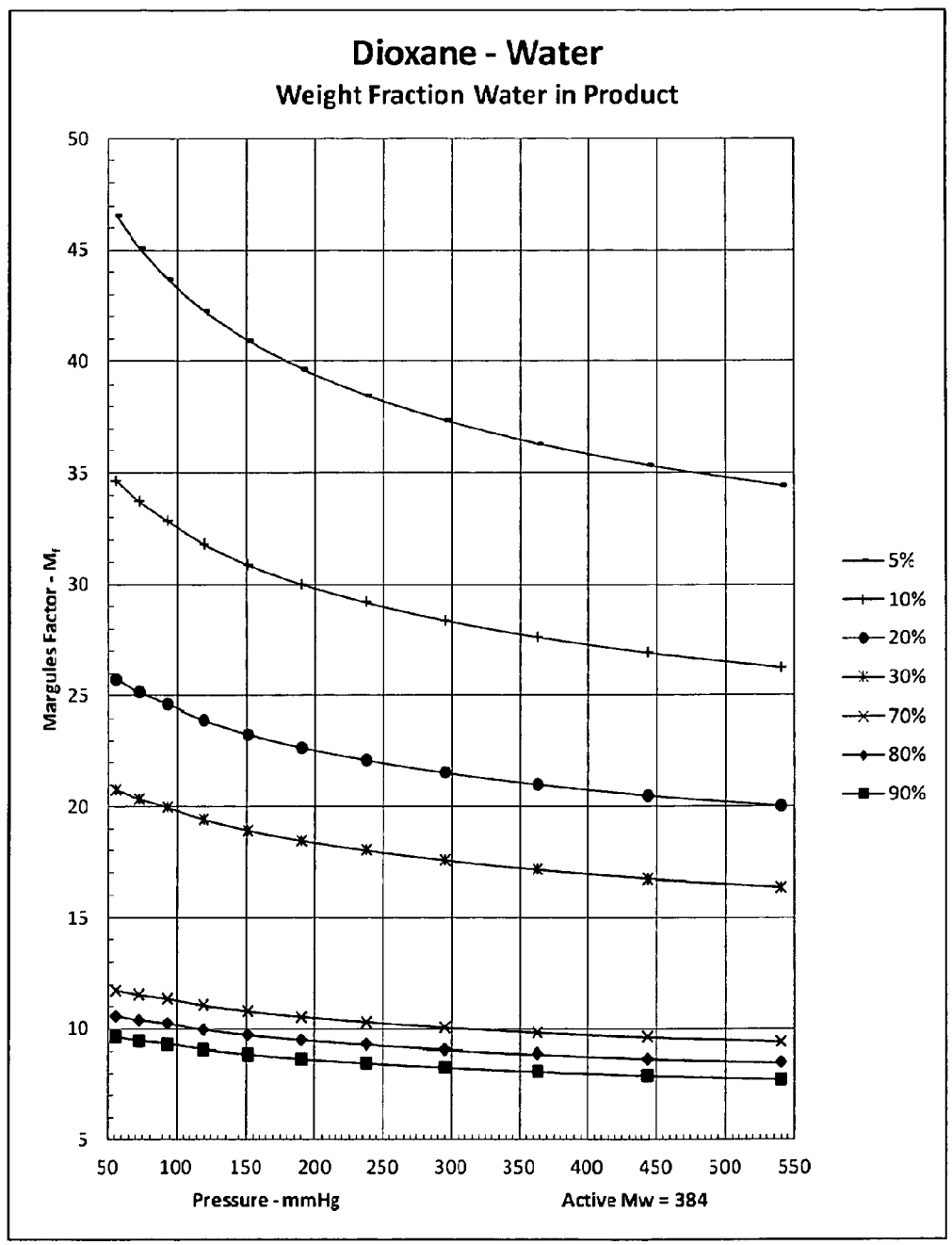
Figure 14:
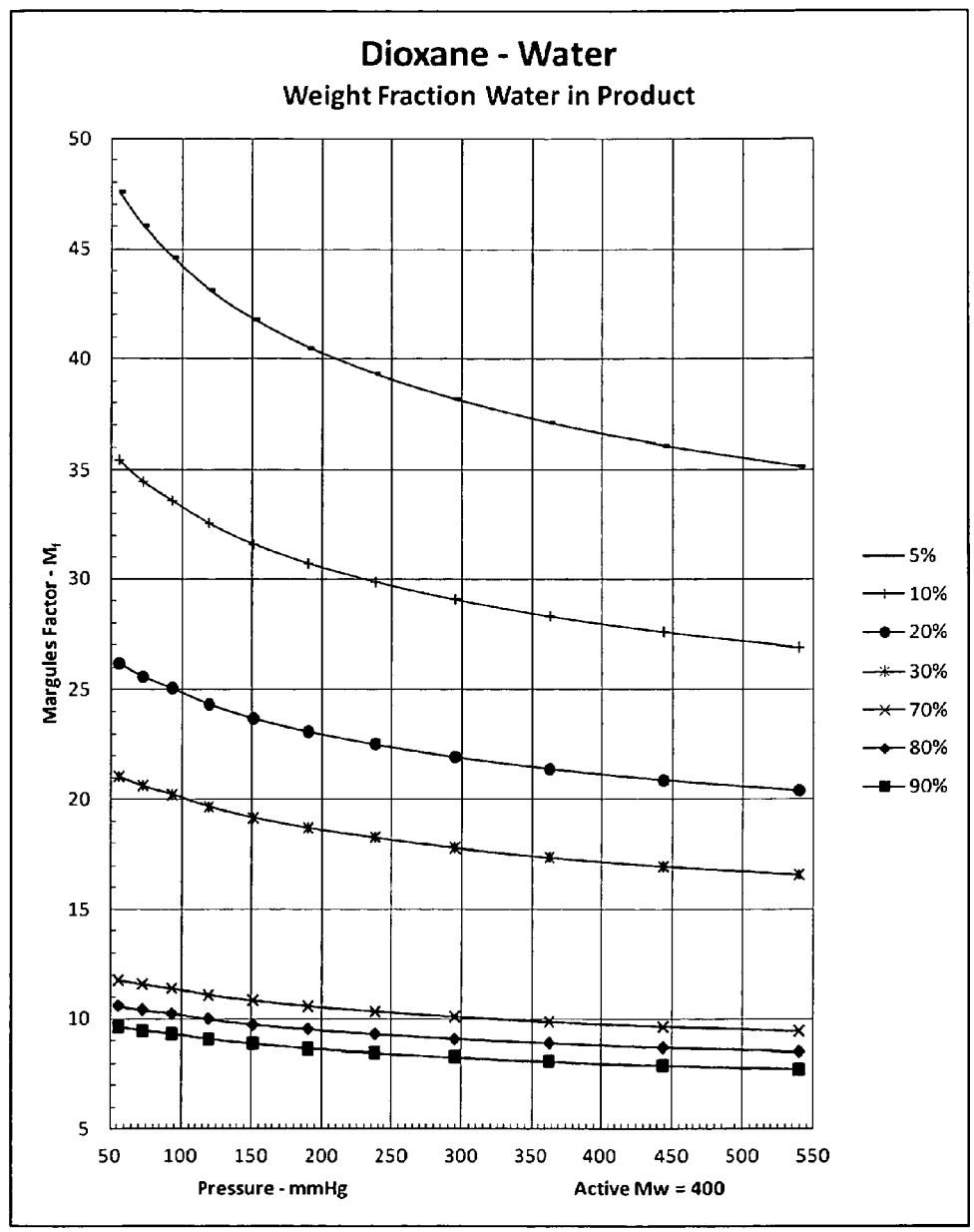
Figure 15:
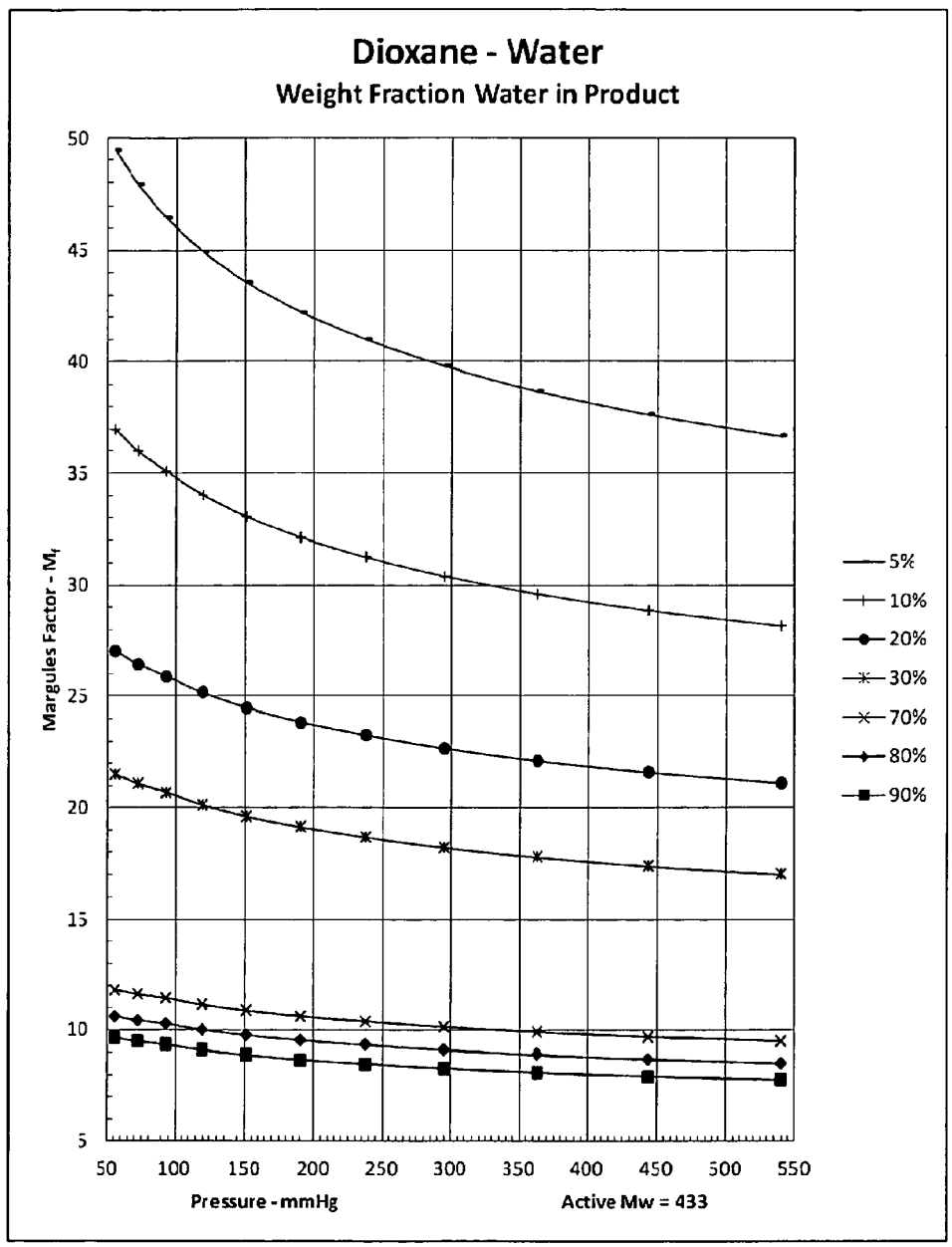
Figure 16:
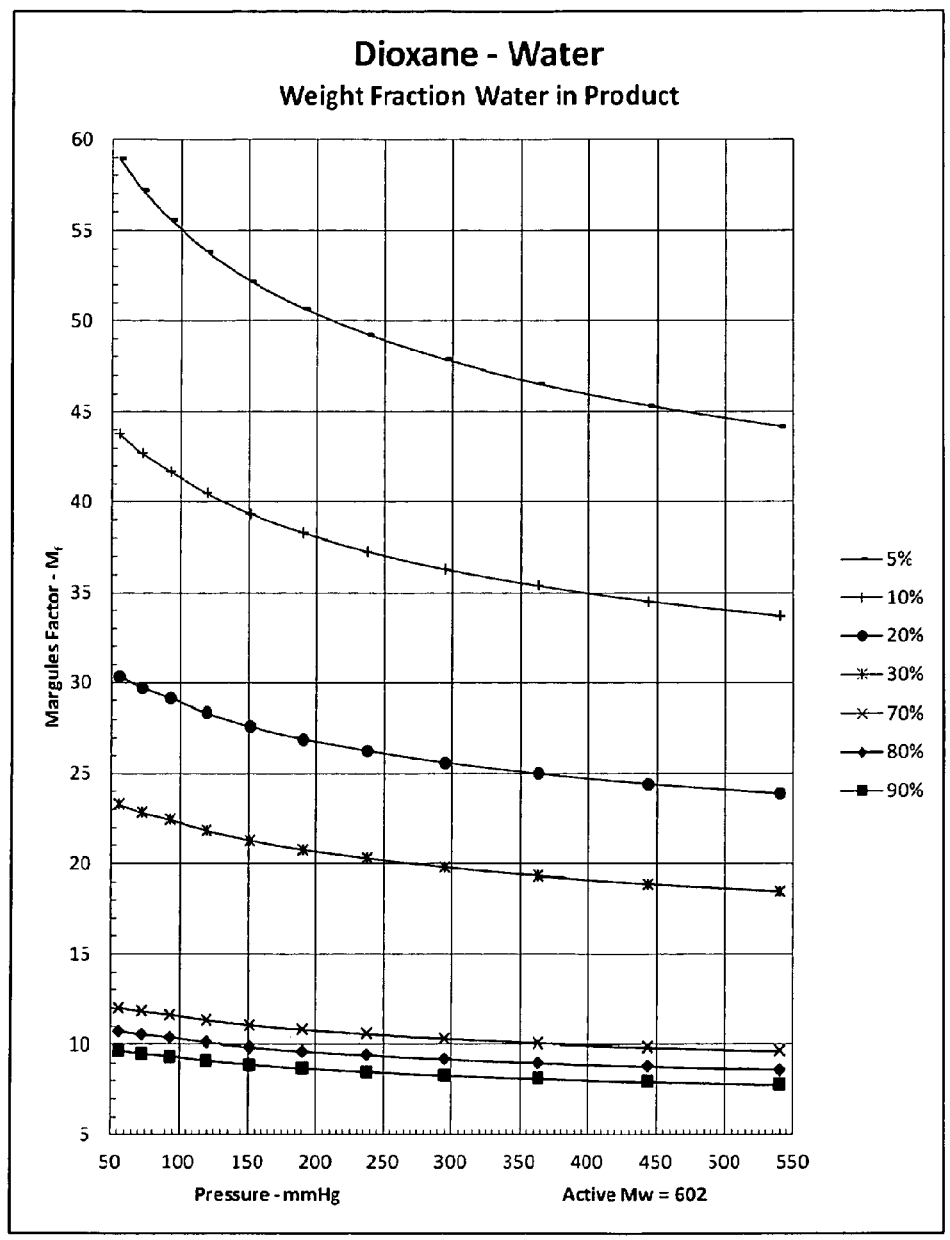

The next graph at FIG. 8 shows values of $I_f$ at different concentrations.

Empirical Model

The foregoing is based on ideal behavior of the binary vapor/liquid system. When compared to actual results, the predicted equilibrium is approximately half of the values necessary to explain empirical data. Dioxane and water are known to not behave in an ideal manner. Margules equations are an empirical method to model binary liquid systems. The following is the same procedure using Margules equations in place of Raoult's Law.

$$x_i \gamma_i V_{p\,i}^0 = p_i = y_i P_T$$

Where $\gamma_i$ is the activity coefficient. Continuing the calculation as above:

$$P_T = \frac{x_i}{y_i}\gamma_i V_{p_i}^0 \qquad\text{Equation 8}$$

$$\frac{x_D}{y_D}\gamma_D V_{PD}^0 = \frac{x_W}{y_W}\gamma_W V_{PW}^0$$

$$y_D = y_W \frac{x_D}{y_W}\gamma_D/\gamma_W V_{PD}^0/V_{PW}^0$$

$$\frac{V_{PD}^0}{V_{PW}^0} = S_f$$

$$y_D = y_W \frac{x_D}{x_W}\gamma_D/\gamma_W S_f:$$

The activity coefficients are:

$$\ln \gamma_d = X_W^2[A_{DW} + 2(A_{WD} - A_{DW})X_D]$$

$$\ln \gamma_W = X_D^2[A_{WD} + 2(A_{DW} - A_{WD})X_W]$$

$$\gamma_D/\gamma_W = e^{X_W^2[A_{DW}+2(A_{WD}-A_{DW})X_D] - X_D^2[A_{WD}+2(A_{DW}-A_{WD})X_W]}$$

We are stripping dioxane attempting to achieve levels at or below 20 ppm weight, for example, while the water content is measured in weight percent. Converting to mole fraction, the values of $x_D$ approach zero and those terms can be cancelled to yield:

$$\gamma_D/\gamma_W = e^{X_W^2[A_{DW}+2(A_{WD}-A_{DW})X_D] - X_D^2[A_{WD}+2(A_{DW}-A_{WD})X_W]}$$

$$\gamma_D/\gamma_W = e^{X_W^2 A_{DW}}$$

Substituting into Equation 8:

$$y_D = y_W \frac{x_D}{x_W} e^{X_W^2 A_{DW}} S_f: \qquad\text{Equation 9}$$

which is the equivalent of Equation 4 in the ideal case.
Published values for $A_{DW}$ are as follows:

| Temperature ° C. | Activity Constant |
|---|---|
| 35 | 1.8253 |
| 50 | 1.8937 |
| 70 | 1.9374 |
| 95 | 1.9783 |

Continuing in the same manner as the ideal case but adding the term for the Margules correction the equations are:

$$ppm_T/ppm_P = S_f e^{X_W^2 A_{DW}}(\%_T/\%_P): \qquad\text{Equation 10}$$

and:

$$D_R = 1 + S_R S_f e^{X_W^2 A_{DW}} 100\%/\%_P \qquad\text{Equation 11}$$

Since the equation can be unwieldy, the last terms of the equation have been incorporated into a Margules factor where:

$$M_f = S_f e^{X_W^2 A_{DW}} 100\%/\%_P$$

To make a new equation:

$$D_R = 1 + S_R M_f: \qquad\text{Equation 12}$$

The graphs at FIGS. 9-16 show the Margules factor for different active concentrations with various active molecular weights. The graphs are duplicated with the first group showing the Margules factor verses temperature of the active and the seconds set verses the flash tank pressure.

Equation 12 has been checked against empirical data for a number of different conditions and materials at different moles of ethoxylation. Several conclusions can be drawn by considering the deviation from theory versus dioxane content of the product. There is a trend for the negative of the error to approach values that are similar to the water content of the paste. So, for paste with 25% moisture, the separation seems to be approaching 75% of theoretical or an error of −25% and 15% paste is approaching 85% of theoretical or an error of −15%. Logically, at 0% water in the paste the dioxane level should be 0 and the error would be 0%. This variance to ideal would be unique for a specific design, in other words, strippers of different lengths or different design principles, as a vacuum neutralizer, would have different efficiencies.

Equation 12 can be modified to reflect what is seen in empirical tests:

$$D_R = (1 + eS_R M_f): \qquad\text{Equation 16}$$

where e is the efficiency of the stripper. A good value to be used on the apparatus described herein is about 75% for a 70% active paste.

Application of Theory and Practical Applications

We consider Equation 11 to see the effect when drying.

$$D_R = 1 + S_R S_f e^{X_W^2 A_{DW}} 100\%/\%_P \qquad\text{Equation 11}$$

The term $\%_P$ is the weight percent of water in the final paste. It is apparent as the amount of water approaches zero, the dioxane reduction ratio approaches infinity. This makes sense since the vapor pressure of dioxane is greater than water, so if all of the water is evaporated, then all of the dioxane will also go into the vapor phase and be removed. This is consistent with experimental data.

If during start-up there is difficulty in reaching dioxane removal levels or if there is a need to increase removal, one course of action is to dry the product slightly. Since the steam ratio is the ratio of steam to the product at the discharge of the tube, drying increases the quantity of steam, decreases the amount of product and increases the steam ratio, $S_R$. Based on Equation 11, low water content of the paste, $100\%/\%_V$, achieves a better reduction. Additionally, it seems that we approach equilibrium in the real world as the moisture level in the product goes down, e increases, Equation 16.

There is another reason to dry the product during stripping. It has been observed that the system more nearly approaches equilibrium when drying. Without intending to be bound by any particular theory, it is believed that there is better contact with the paste throughout the film as water vaporizes in the film.

As described herein, it is desirable to include a dilution system to adjust the final product concentration. In principle, it is desirable to neutralize to higher solids (e.g., in a range of 68 wt. % to 85 wt. %), strip dioxane and dry/concentrate the paste, and then dilute the paste, in order to minimize the amount of steam to attain a specific level of reduction. The restriction on doing this is the viscosity of the neutralized paste and the consequent handling problems.

There can be a significant cost savings possible by using stripping/drying systems described herein in series or by campaigning (running the product through the unit multiple times) through a single stage. There can be a much less dramatic improvement in steam consumption with three stages compared to two stages, but there are still circumstances where three or more stages may be desirable, particularly in the campaign mode. That is, when dioxane reductions in excess of what is normal for one stage are needed as might happen during a process up-set. In this case the dioxane reduction ratio would be $D_R^n$ where $D_R$ is the dioxane ratio of one stage and n is the number of stages. As an example assuming the one stage yields a reduction of 5:1, two stages would yield 25:1 and three stages would yield 125:1.

EXAMPLES

The invention is further described and illustrated by the following examples which are not intended to be limiting. Equipment conditions, processing conditions, feedstock conditions, and product conditions are provided for examples 1-17 in the table which is split between FIGS. 17a and 17b. In Examples 1 and 2, the method used a 10 foot (3 meter), 3-tube bundle wherein the inside tube diameter was 0.4 inch (1 cm) followed by a 10 foot (3 meter) extension of 2 inch (5 cm) inner diameter pipe. In the remainder of the Examples, 3-17, the method used a single 10 foot (3 meter), 3-tube bundle wherein the inside tube diameter was 0.4 inch (1 cm).

The examples show that dioxane reduction ratios exceeding 100 have been achieved according to the process described herein. The Examples also show that while injection of additional stripping steam is particularly advantageous, flashing of steam from water already present in the feedstock can achieve a dioxane reduction ratio as high as about 7 (see Example 16). The examples also show the beneficial effect of drying the product to a relatively high degree. For example, in comparing Examples 1 and 2, the water content of the concentrated paste product was 10% for Example 1 and 5% for Example 2. The 1,4-dioxane reduction ratio was 46 for Example 1 and 103 (more than double) for Example 2, whereas the injection steam remained constant but the drying temperature was increased.

The embodiments described in the following paragraphs are specifically contemplated.

1. A method of removing dioxane from an aqueous alkoxylated fatty alcohol sulfate paste, comprising:
   pumping a dioxane-containing aqueous paste feedstock to an inlet of an evaporator;
   supplying heat to the paste in the evaporator; and
   reducing the vapor pressure in the evaporator;
to vaporize dioxane and water from the paste and thereby concentrate the paste, wherein the wt. % increase of the active sulfonate following concentration, based on the total weight of the paste, is at least 5 wt. %, and collecting the resulting concentrated product.

2. The process according to paragraph 1, further comprising diluting the concentrated product with water.

3. The process according to paragraph 2, comprising diluting the concentrated product to a concentration of about 65 wt. % to about 76 wt. % active sulfate.

4. The process according to paragraph 2 or 3, further comprising adjusting the pH of the diluted product by addition of a neutralizing agent.

5. The process according to paragraph 1, wherein the evaporator comprises a wiped film evaporator.

6. The process according to paragraph 1, wherein the evaporator comprises a channel and further comprising preheating the dioxane-containing paste feedstock to a temperature wherein water would flash from the paste, and selectively applying pressure to the paste to avoid vaporization of water; pumping the paste to an inlet of the channel under a pressure selected to avoid flashing of water; introducing the paste into the channel; supplying heat to the paste in the channel and selectively reducing the pressure along the channel resulting in the flashing of dioxane and water components of the paste, wherein vapor liberated during the flashing acts as a motive force to move the increasingly viscous paste along the channel; collecting the resulting concentrated product and vaporized dioxane and water components in a separation vessel disposed downstream of an outlet of the channel, wherein the separation vessel operates at a pressure less than an operating pressure of the outlet of each channel; and venting the vaporized dioxane and water components from the separation vessel from an overhead vapor outlet and discharging the residual paste composition from the bottom of the separation vessel.

7. The process of any one of the preceding paragraphs, wherein the feedstock paste comprises an ethoxylated fatty alcohol sulfate.

8. The process according to any one of the preceding paragraphs, wherein the feedstock is preheated to a temperature in a range of about 185° F. to 265° F. (85° C. to 129° C.), for example 240° F. (116° C.).

9. The process according to any one of the preceding paragraphs, wherein the evaporator is heated to a temperature in a range of about 200° F. to 265° F. (93° C. to 129° C.), for example 240° F. (116° C.).

10. The process of any one of the preceding paragraphs, wherein the vapor pressure in the evaporator or collection vessel is less than 1 bar absolute.

11. The process of paragraph 10, wherein the pressure is in a range of 50 Torr to 300 Torr.

12. The process according to any one of the preceding paragraphs, wherein the concentrated product comprises 76 wt. % to 99 wt. % active ethoxylated fatty alcohol sulfate.

13. The process according to any one of the preceding paragraphs, wherein the concentrated product has a water content of 25 wt. % or less, or 15 wt. % or less, or 5 wt. % or less, or 2 wt. % or less.

14. The process according to any one of the preceding paragraphs, wherein the wt. % increase of the active sulfonate following concentration, based on the total weight of the paste, is at least 10 wt. %.

15. The process according to paragraph 13, wherein the concentrated product comprises 3-mol ethoxylated fatty alcohol sulfate and the concentrated product comprises 76 wt. % to 88 wt. % active.

16. The process according to paragraph 13, wherein the concentrated product comprises 7-mol ethoxylated fatty alcohol sulfate and the concentrated product comprises 76 wt. % to 95 wt. % active.

17. The process according to any one of the preceding paragraphs, wherein the ratio of dioxane concentration on 100% active basis in the feedstock paste compared to the product paste is at least 7:1.

18. The process according to any one of the preceding paragraphs, wherein the dioxane content of the concentrated product is less than 20 ppm on 100% active matter basis.

19. The process according to any one of the preceding paragraphs, wherein the dioxane is 1,4-dioxane.

20. The process according to any one of the preceding paragraphs, further injecting a vapor into the evaporator.

21. The process according to paragraph 20, wherein the vapor is steam.

22. The process according to paragraph 21, wherein the feedstock paste is an ethoxylated fatty alcohol sulfate paste and the mass ratio of injected steam to active ethoxylated fatty alcohol sulfate is in a range of 0.1 to 1.

23. A system for removing dioxane from an aqueous paste, comprising: a heated evaporator channel having an inlet and an outlet, a liquid feed pump in fluid communication with the inlet of the evaporator channel, a separation vessel having an inlet in fluid communication with the outlet of the evaporator channel and an outlet in fluid communication with a diluter, and a vacuum pump in fluid communication with the separation vessel.

24. A system for removing dioxane from an aqueous paste, comprising: a wiped film evaporator having a feed inlet, a concentrate product outlet, and at least one vapor outlet, a liquid feed pump in fluid communication with the inlet of the wiped film evaporator, a diluter in fluid communication with the concentrate product outlet, and a vacuum pump in fluid communication with the wiped film evaporator vapor outlet.

The foregoing description is given for clearness of understanding only, and no unnecessary limitations should be understood therefrom, as modifications within the scope of the invention will be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A method of removing dioxane from an aqueous alkoxylated fatty alcohol sulfate paste, comprising:
   pumping a dioxane-containing aqueous paste feedstock to an inlet of an evaporator;
   supplying heat to the paste in the evaporator; and
   reducing the vapor pressure in the evaporator;
to vaporize dioxane and water from the paste and thereby concentrate the paste, wherein the wt. % increase of the active sulfate following concentration, based on the total weight of the paste, is at least 5 wt. %, and collecting the resulting concentrated product.

2. The process according to claim 1, further comprising diluting the concentrated product with water and adjusting the pH of the diluted product by addition of a neutralizing agent.

3. The process according to claim 1, wherein the evaporator comprises a wiped film evaporator.

4. The process according to claim 1, wherein the evaporator comprises a channel and further comprising preheating the dioxane-containing paste feedstock to a temperature wherein water would flash from the paste, and selectively applying pressure to the paste to avoid vaporization of water; pumping the paste to an inlet of the channel under a pressure selected to avoid flashing of water; introducing the paste into the channel; supplying heat to the paste in the channel and selectively reducing the pressure along the channel resulting in the flashing of dioxane and water components of the paste, wherein vapor liberated during the flashing acts as a motive force to move the increasingly viscous paste along the channel; collecting the resulting concentrated product and vaporized dioxane and water components in a separation vessel disposed downstream of an outlet of the channel, wherein the separation vessel operates at a pressure less than an operating pressure of the outlet of each channel; and venting the vaporized dioxane and water components from the separation vessel from an overhead vapor outlet and discharging the residual paste composition from the bottom of the separation vessel.

5. The process according to claim 1, wherein the feedstock paste comprises an ethoxylated fatty alcohol sulfate.

6. The process according to claim 1, wherein the feedstock is preheated to a temperature in a range of about 185° F. to 265° F. (85° C. to 129° C.), for example 240° F. (116° C.).

7. The process according to claim 1, wherein the evaporator is heated to a temperature in a range of about 200° F. to 265° F. (93° C. to 129° C.), for example 240° F. (116° C.).

8. The process according to claim 1, wherein the pressure of the vapor in the evaporator or collection vessel is less than 1 bar absolute.

9. The process according to claim 8, wherein the pressure is in a range of 50 Torr to 300 Torr.

10. The process according to claim 1, wherein the concentrated product comprises 76 wt. % to 99 wt. % active ethoxylated fatty alcohol sulfate.

11. The process according to claim 1, wherein the concentrated product has a water content of 25 wt. % or less.

12. The process according to claim 1, wherein the wt. % increase of the active sulfate following concentration, based on the total weight of the paste, is at least 10 wt. %.

13. The process according to claim 12, wherein the concentrated product comprises 3-mol ethoxylated fatty alcohol sulfate and the concentrated product comprises 76 wt. % to 88 wt. % active.

14. The process according to claim 12, wherein the concentrated product comprises 7-mol ethoxylated fatty alcohol sulfate and the concentrated product comprises 85 wt. % to 95 wt. % active.

15. The process according to claim 1, wherein the ratio of dioxane concentration on 100% active basis in the feedstock paste compared to the product paste is at least 7:1.

16. The process according to claim 1, wherein the dioxane content of the concentrated product is less than 20 ppm on 100% active matter basis.

17. The process according to claim 1, wherein the dioxane is 1,4-dioxane.

18. The process according to claim 1, further injecting a vapor into the evaporator.

19. The process according to claim 18, wherein the vapor is steam.

20. The process according to claim 19, wherein the feedstock paste is an ethoxylated fatty alcohol sulfate paste and the mass ratio of injected steam to active ethoxylated fatty alcohol sulfate is in a range of 0.1 to 1.

21. The process according to claim 5, wherein the feedstock paste comprises a sodium ethoxysulfate.

22. The process according to claim 1, comprising diluting the concentrated product with water to a concentration of about 65 wt.% to about 80 wt.% active sulfate.

23. The process according to claim 1, comprising diluting the concentrated product with water to a concentration of about 68 wt.% to about 85 wt.% solids.

24. The process according to claim 10, wherein the concentrated product comprises 80 wt.% to 95 wt.% active ethoxylated fatty alcohol sulfate.

25. The process according to claim 11, wherein the concentrated product has a water content of 15 wt.% or less.

26. The process according to claim 25, wherein the concentrated product has a water content of 5 wt.% or less.

27. The process according to claim 26, wherein the concentrated product has a water content of 2 wt.% or less.

28. The process according to claim 13 wherein the wherein the concentrated product comprises 3-mol ethoxylated fatty alcohol sulfate and the concentrated product comprises 80 wt.% to 88 wt.% active.

29. The process according to claim 1, wherein the ratio of dioxane concentration on 100% active basis in the feedstock paste compared to the product paste is at least 4:1.

30. The process according to claim 1, wherein the ratio of dioxane concentration on 100% active basis in the feedstock paste compared to the product paste is greater than 7:1.

31. The process according to claim 1, wherein the ratio of dioxane concentration on 100% active basis in the feedstock paste compared to the product paste is at least 20:1.

32. The process according to claim 16, wherein the dioxane content of the concentrated product is less than 10 ppm on 100% active matter basis.

33. The process according to claim 19, wherein the feedstock paste is an ethoxylated fatty alcohol sulfate paste and the mass ratio of steam to total paste mass is in a range of about 0.1 to 1.

34. The process according to claim 1, further comprising sulfating an alkoxylated fatty alcohol with a sulfur trioxide gas concentration of greater than 2.5%, to produce the alkoxylated fatty alcohol sulfate paste.

35. The process according to claim 34, wherein the concentration of sulfur trioxide gas is at least 3.5%.

36. The process according to claim 1, further comprising sulfating an alkoxylated fatty alcohol with a mole ratio of sulfur trioxide gas to alkoxylated fatty alcohol of at least 1.00, to produce the alkoxylated fatty alcohol sulfate paste.

37. The method of claim 4, further comprising diluting the collected concentrated product to a concentration of about 65 wt.% to about 76 wt.% active sulfate; wherein the evaporator is heated to a temperature in a range of about 200° F. to 265° F. (93° C. to 129° C.); and wherein the dioxane is 1,4-dioxane.

38. The process according to claim 37, further comprising sulfating an alkoxylated fatty alcohol with a sulfur trioxide gas concentration of greater than 2.5%, to produce the alkoxylated fatty alcohol sulfate paste.

39. The process according to claim 37, further comprising sulfating an alkoxylated fatty alcohol with a mole ratio of sulfur trioxide gas to alkoxylated fatty alcohol of at least 1.00, to produce the alkoxylated fatty alcohol sulfate paste.

40. The process according to any one of claims 1, 3 to 20, 21, or 24-36, further comprising diluting the concentrated product with water.

41. The process according to claim 2, comprising diluting the concentrated product to a concentration of about 65 wt. % to about 76 wt. % active sulfate.

* * * * *

UNITED STATES PATENT AND TRADEMARK OFFICE
CERTIFICATE OF CORRECTION

PATENT NO. : 8,865,928 B2
APPLICATION NO. : 14/048600
DATED : October 21, 2014
INVENTOR(S) : Walter A. Jessup et al.

It is certified that error appears in the above-identified patent and that said Letters Patent is hereby corrected as shown below:

In the Drawings:

At Figure 8, "Ideal Sedparation Factor -- $I_f$" should be -- Ideal Separation Factor – $I_f$ --

In the Specification:

At Column 11, line 8, "dried up 95 wt% active" should be -- dried up to 95 wt% active --

At Column 11, line 35, "1,4-dioxiane" should be -- 1,4-dioxane --

At Column 18, line 7, "system 10" should be -- system 210 --

At Column 18, line 58, "Air is air" should be -- A is air --

At Column 18, line 67, "dioxane of the feed" should be -- dioxane content of the feed --

Signed and Sealed this
Eighteenth Day of August, 2015

Michelle K. Lee
*Director of the United States Patent and Trademark Office*